United States Patent
Sudo et al.

(10) Patent No.: US 11,622,792 B2
(45) Date of Patent: Apr. 11, 2023

(54) ROD GROUP, ARCUATE ROD, S-SHAPED ROD, SPINE STABILIZATION SYSTEM, AND ROD MANUFACTURING METHOD

(71) Applicants: National University Corporation Hokkaido University, Sapporo (JP); Robert Reid, Inc., Tokyo (JP)

(72) Inventors: Hideki Sudo, Sapporo (JP); Satoshi Kanai, Sapporo (JP); Terufumi Kokabu, Sapporo (JP); Yuichiro Abe, Sapporo (JP); Tsuyoshi Segawa, Tokyo (JP)

(73) Assignees: NATIONAL UNIVERSITY CORPORATION HOKKAIDO UNIVERSITY, Sapporo (JP); ROBERT REID INC., Tokyo (JP)

( * ) Notice: Subject to any disclaimer, the term of this patent is extended or adjusted under 35 U.S.C. 154(b) by 804 days.

(21) Appl. No.: 16/337,450

(22) PCT Filed: Aug. 1, 2018

(86) PCT No.: PCT/JP2018/028933
§ 371 (c)(1),
(2) Date: Mar. 28, 2019

(87) PCT Pub. No.: WO2019/167305
PCT Pub. Date: Sep. 6, 2019

(65) Prior Publication Data
US 2021/0330360 A1    Oct. 28, 2021

Related U.S. Application Data

(63) Continuation-in-part of application No. PCT/JP2018/028933, filed on Aug. 1, 2018.

(30) Foreign Application Priority Data

Feb. 28, 2018   (JP) .............................. JP2018-034840

(51) Int. Cl.
*A61B 17/88* (2006.01)
*A61B 17/70* (2006.01)
*A61B 17/00* (2006.01)

(52) U.S. Cl.
CPC ...... *A61B 17/7011* (2013.01); *A61B 17/7085* (2013.01); *A61B 2017/00526* (2013.01)

(58) Field of Classification Search
CPC ............ A61B 17/7011; A61B 17/7085; A61B 2017/00526

(Continued)

(56) References Cited

U.S. PATENT DOCUMENTS 5,133,716 A * 7/1992 Plaza ................. A61B 17/7053
606/250
5,951,553 A   9/1999 Betz et al.
(Continued)

FOREIGN PATENT DOCUMENTS

| JP | 2016093497 A | 5/2016 |
| JP | 2016-129670 A | 7/2016 |
| WO | 2010/011535 A1 | 1/2010 |

*Primary Examiner* — Eduardo C Robert
*Assistant Examiner* — David C Comstock
(74) *Attorney, Agent, or Firm* — Tarolli, Sundheim, Covell & Tummino LLP

(57) ABSTRACT

A rod group includes a plurality of first rods that has an arcuate first curve, the first rods having mutually different lengths; and a plurality of second rods that has an S-shaped second curve, the second rods having mutually different lengths. The first rods and the second rods have shapes for treatment of scoliosis by (i) guiding the postoperative apex of the thoracic kyphosis to be located at the thoracic vertebrae T6 to T8, and (ii) guiding a postoperative apex of the thoracic kyphosis to be located at a position different from a preoperative apex of the thoracic kyphosis and the second (Continued)

rod each have a shape extending along an anatomically normal spinal column arrangement.

8 Claims, 32 Drawing Sheets

(58) Field of Classification Search
USPC .................................... 606/261, 264, 279
See application file for complete search history.

(56) References Cited

U.S. PATENT DOCUMENTS

| | | |
|---|---|---|
| 10,092,328 B2 | 10/2018 | Sharifi-Mehr et al. |
| 10,314,657 B2 * | 6/2019 | Mosnier .................. G06T 7/337 |
| 2005/0277934 A1 | 12/2005 | Vardiman |
| 2009/0093843 A1 | 4/2009 | Lemoine |
| 2009/0254326 A1 * | 10/2009 | Isaacs .................... B21D 7/063 |
| | | 703/11 |
| 2010/0106193 A1 * | 4/2010 | Barry .................. A61B 17/701 |
| | | 606/264 |
| 2013/0096624 A1 | 4/2013 | Di Lauro |
| 2013/0345757 A1 * | 12/2013 | Stad .................. A61B 17/7011 |
| | | 606/279 |
| 2014/0222078 A1 | 8/2014 | Spine |
| 2016/0199101 A1 * | 7/2016 | Sharifi-Mehr ..... A61B 17/7002 |
| | | 606/258 |
| 2016/0242857 A1 * | 8/2016 | Scholl ................ A61B 17/7001 |
| 2016/0310170 A1 * | 10/2016 | Carls ................. A61B 17/7022 |
| 2017/0360493 A1 * | 12/2017 | Zucker .................. A61B 5/107 |
| 2018/0014860 A1 * | 1/2018 | Stein .................. A61B 17/7025 |

* cited by examiner

Second ROD    ROD LENGTH 230-260

Second ROD    ROD LENGTH 260-290

Second ROD    ROD LENGTH 290-320

Second ROD　　ROD LENGTH 320-350

Second ROD   ROD LENGTH 350-380

FIG. 31
FIG. 32
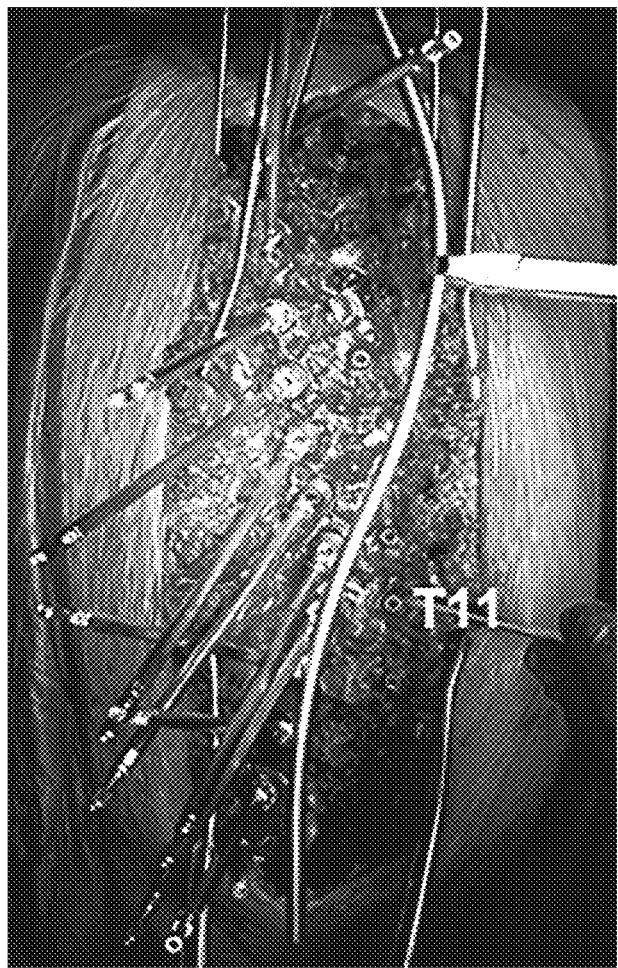
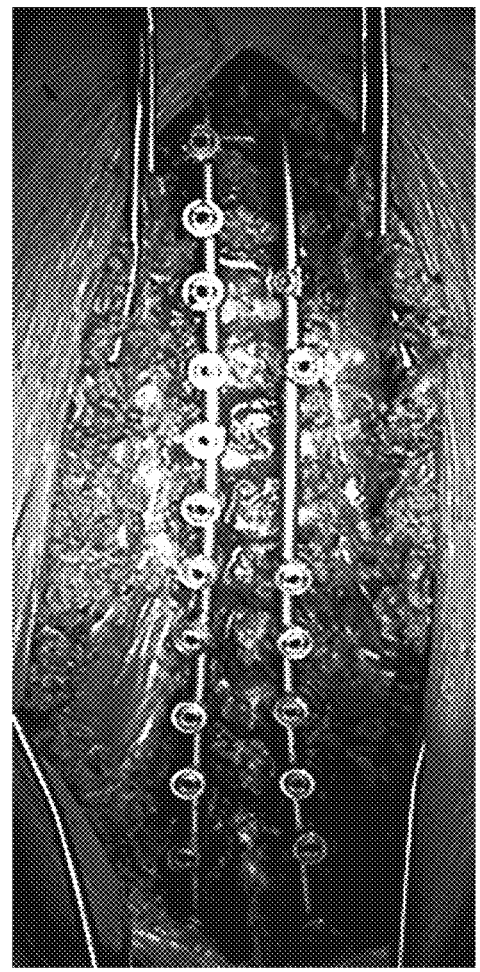

ROD GROUP, ARCUATE ROD, S-SHAPED ROD, SPINE STABILIZATION SYSTEM, AND ROD MANUFACTURING METHOD

TECHNICAL FIELD

The present disclosure relates to a rod group, an arcuate rod, an S-shaped rod, a spine stabilization system, and a rod manufacturing method, in particular, to a rod group, an arcuate rod, an S-shaped rod, a spine stabilization system, and a rod manufacturing method, which are used for acquiring an anatomically normal spinal column arrangement.

BACKGROUND ART

The spinal column, in principle, consists of a plurality of vertebrae (seven cervical vertebrae, twelve thoracic vertebrae, five lumbar vertebrae, a sacrum, and a coccyx) and intervertebral disks that lie between the vertebrae and join the vertebrae. In a normal condition, the spinal column is generally straight in a coronal direction and generally S-shaped in a sagittal direction where the cervical vertebrae and lumbar vertebrae curve to convex forward and the thoracic vertebrae and sacrum curve to convex backward.

Spinal deformity correction and fusion is a surgery for correcting and fusing a deformed spinal column, and is, in general, performed for treatment of idiopathic scoliosis. Idiopathic scoliosis, a condition that causes deformation of the spinal column, includes scoliosis and kyphosis. Scoliosis is a condition that causes the spinal column to curve sideways or to twist. Kyphosis is a condition that causes the angle of thoracic kyphosis to be excessively large or a condition that causes a loss of lumbar lordosis and makes the lumbar kyphotic.

In the spinal deformity correction and fusion, the spinal column is corrected and fused by maintaining rods made mainly from materials, such as titanium alloy and cobalt chromium alloy, with screws and the like screwed into the vertebrae. The rods are usually manually bent by a doctor using a variety of tools during surgery. The posture of the spinal column after correction is generally determined by the shapes of the bent rods. Thus, how the rods are bent is an important factor in the spinal deformity correction and fusion, which depends on expertise and intuition of a surgeon.

In a system for designing and manufacturing a surgical implant as described in Cited Literature 1, a spatial relationship among coupling device attachment elements (for example, screws) to be implanted in a corporeal structure is determined, from which rod bending parameters are determined. Rods to be used for spinal deformity correction and fusion are obtained by bending straight rods using bending tools based on the determined bending parameters.

CITATION LIST

Patent Literature

Patent Literature 1: Japanese Patent No. 5572898

SUMMARY OF INVENTION

Technical Problem

In the system for designing and manufacturing a surgical implant described in Cited Literature 1, straight rods are bent manually by a doctor using bending tools during surgery, thus, a spinal column arrangement that is anatomically original for a patient may not be acquired when the shapes of the bent rods do not match the spinal column of the patient.

The present disclosure has been contrived in consideration of the above problem. The objective of the present disclosure is to provide a rod group, an arcuate rod, an S-shaped rod, a spine stabilization system, and a rod manufacturing method that are used for the purpose of acquiring an anatomically normal spinal column arrangement in spinal deformity correction and fusion.

Solution to Problem

To achieve the above objective, a rod group according to a first aspect of the present disclosure includes: a plurality of first rods that has an arcuate first curve, the first rods having mutually different lengths; and a plurality of second rods that has an S-shaped second curve, the second rods having mutually different lengths, wherein the first rods have (i) in a shape extending along thoracic kyphosis of an anatomically normal spinal column arrangement, a curved section and a straight section to be attached to thoracic vertebrae, or (ii) in a shape extending along thoracic kyphosis of an anatomically normal spinal column arrangement, a curved section and reverse curved section to be attached to the thoracic vertebrae, the second rods have (i) in a shape extending along thoracic kyphosis of an anatomically normal spinal column arrangement, a first curved section to be attached to the thoracic vertebrae, and (ii) in a shape extending along lumbar lordosis of an anatomically normal spinal column arrangement, a second curved section to be attached to lumbar vertebrae, and the first rods and the second rods have shapes for treatment of scoliosis by (i) guiding the postoperative apex of the thoracic kyphosis to be located at the thoracic vertebrae T6 to T8, and (ii) guiding a postoperative apex of the thoracic kyphosis to be located at a position different from a preoperative apex of the thoracic kyphosis and the second rod each have a shape extending along an anatomically normal spinal column arrangement.

To achieve the above objective, an arcuate rod according to a second aspect of the present disclosure is an arcuate rod for treatment of scoliosis and having that has an arcuate curve, wherein the arcuate rod has (i) in a shape extending along thoracic kyphosis of an anatomically normal spinal column arrangement, a curved section and a straight section to be attached to thoracic vertebrae, or (ii) in a shape extending along thoracic kyphosis of an anatomically normal spinal column arrangement, a curved section and reverse curved section to be attached to the thoracic vertebrae, and the arcuate rod has a shape for treatment of scoliosis by (i) guiding a postoperative apex of the thoracic kyphosis to be located at the thoracic vertebrae T6 to T8, and (ii) guiding the postoperative apex of the thoracic kyphosis to be located at a position different from a preoperative apex of the thoracic kyphosis.

To achieve the above objective, an S-shaped rod according to a third aspect of the present disclosure is an S-shaped rod for treatment of scoliosis and having that has an S-shaped curve comprising: a first curved section; and a second curved section that curves in an opposite direction to the first curved section, wherein the first curved section has a shape extending along thoracic kyphosis of an anatomically normal spinal column arrangement, and the second curved section has a shape extending along lumbar lordosis of an anatomically normal spinal column arrangement the S-shaped rod has (i) in a shape extending along thoracic kyphosis of an anatomically normal spinal column arrangement, a first curved section to be attached to thoracic vertebrae, and (ii) in a shape extending along lumbar lordosis of an anatomically normal spinal column arrangement, a second curved section to be attached to lumbar vertebrae, and the S-shaped rod has a shape for (i) guiding the postoperative apex of the thoracic kyphosis to be located at the thoracic vertebrae T6 to T8, and (ii) guiding the postoperative apex of the thoracic kyphosis to be located at a position different from a preoperative apex of the thoracic kyphosis.

To achieve the above objective, a spine stabilization system according to a fourth aspect of the present disclosure includes: the arcuate rod; and a plurality of coupling device attachment elements for attaching the arcuate rod to a spinal column.

To achieve the above objective, a spine stabilization system according to a fifth aspect of the present disclosure includes: the S-shaped rod; and a plurality of coupling device attachment elements for attaching the S-shaped rod to a spinal column.

To achieve the above objective, a rod manufacturing method according to a sixth aspect of the present disclosure includes: a rod data acquisition step of acquiring data indicating a plurality of rod shapes that was bent into shapes extending along anatomically normal spinal column arrangements: a length classification step of classifying data indicating the rod shapes acquired at the rod data acquisition step into groups of rod lengths with a difference of reference length; a rod shape acquisition step of acquiring data indicating best-fit curves from the rod shapes included in groups classified at the length classification step; and a rod making step of making rods used in spinal deformity correction and fusion, according to the best-fit curves acquired at the rod shape acquisition step.

To achieve the above objective, a method for treatment of scoliosis according to a seventh aspect of the present disclosure includes: a prediction step of predicting an anatomically normal spinal column arrangement without thoracic idiopathic scoliosis for a patient with thoracic idiopathic scoliosis; a rod attachment step of attaching to the spinal column of the patient a pair of rods having shapes extending along the spinal column arrangement predicted in the prediction step; a rod rotation step of rotating the attached pair of rods; wherein the method guides the postoperative apex of the thoracic kyphosis to the thoracic vertebrae T6 to T8 and guides the postoperative apex to a position different from a preoperative apex of the thoracic kyphosis.

Advantageous Effects of Invention

According to the present disclosure, an anatomically normal spinal column arrangement can be acquired in spinal deformity correction and fusion.

BRIEF DESCRIPTION OF DRAWINGS

FIG. 31 is an intraoperative photograph of attaching the first rods to the spinal column of a patient using pedicle screws according to the example of the present disclosure;

FIG. 32 is a photograph illustrating a state where the first rods are simultaneously rotated according to the example of the present disclosure;

DESCRIPTION OF EMBODIMENTS

The following will describe a rod group and a spine stabilization system to be used in spinal deformity correction and fusion according to the embodiment of the present disclosure with reference to the drawings.

Figure 1A:
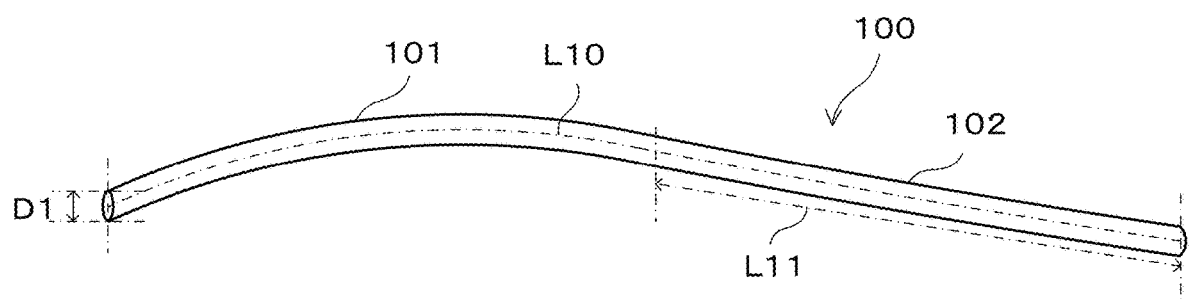
FIG. 1A is a diagram illustrating a first rod to be used for spinal deformity correction and fusion according to the embodiment of the present disclosure.
Figure 1B:
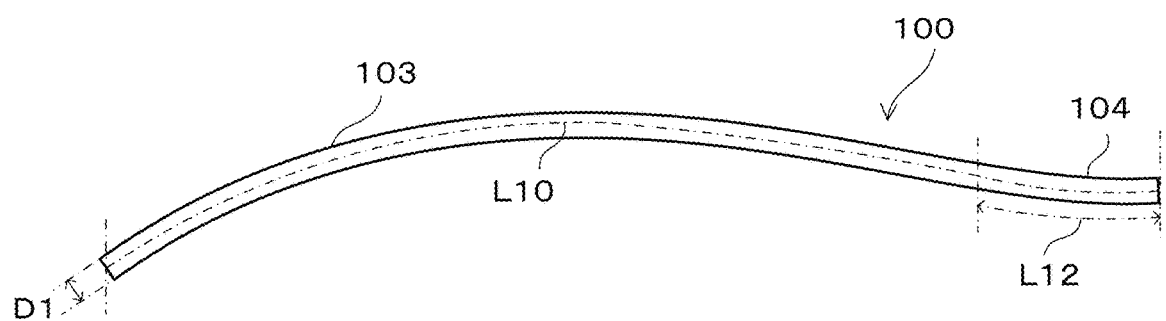
FIG. 1B is a diagram illustrating a first rod to be used for spinal deformity correction and fusion according to the embodiment of the present disclosure.
Figure 1C:
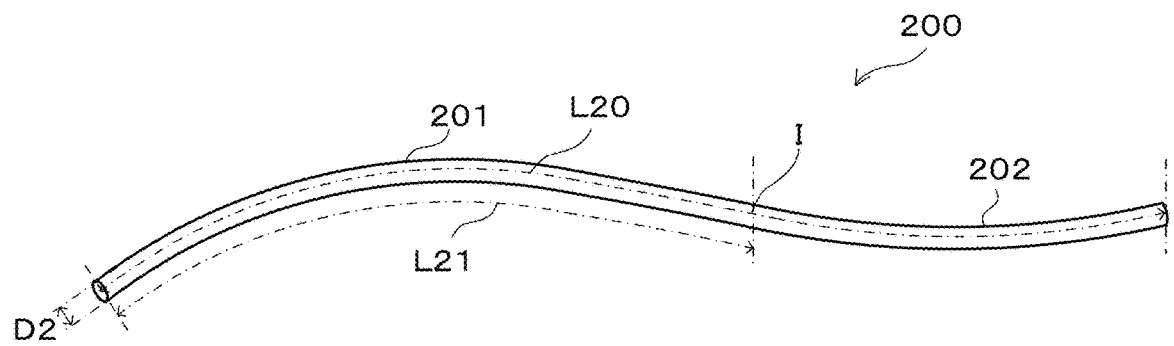
FIG. 1C is a diagram illustrating a second rod to be used for spinal deformity correction and fusion according to the embodiment of the present disclosure.
Figure 3:
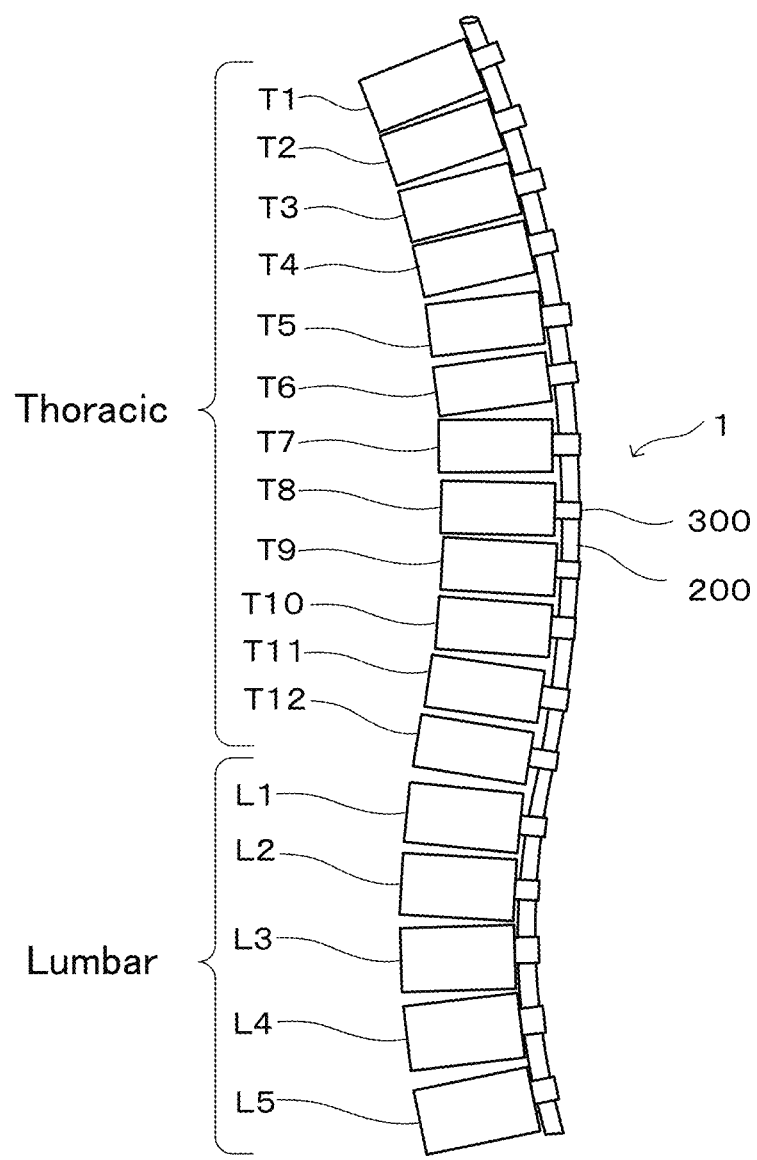
FIG. 3 is a diagram illustrating a state where the second rod is used in spinal deformity correction and fusion and is attached to the spinal column according to the embodiment of the present disclosure.

The rod group to be used in spinal deformity correction and fusion according to the embodiment of the present disclosure includes a first rod (an arcuate rod) 100 that has an arcuate first curve illustrated in FIGS. 1A and 1B and a second rod (an S-shaped rod) 200 that has an S-shaped second curve illustrated in FIG. 1C. The first rod 100 and the second rod 200 each have a shape extending along an anatomically normal spinal column arrangement. The spine stabilization system 1, as illustrated in FIG. 3, includes the first rods 100 or the second rods 200 and pedicle screws (coupling device attachment elements) 300. In the spine stabilization system 1, the first rods 100 or the second rods 200 are attached to the spinal column of a patient using pedicle screws 300 screwed in the vertebrae so as to correct the spinal column to a normal or nearly normal state and provide an anatomically normal spinal column arrangement after the surgery. Note that the anatomically normal spinal column arrangement refers to a state where the spinal column has thoracic kyphosis (TK) and lumbar lordosis and the apex of the TK is located at T6 to T8.

The first rod 100 has a curved section 101 and a straight section 102 as illustrated in FIG. 1A or has a curved section 103 and a reverse curved section 104 that has a curve in an opposite direction to the curved section 103 as illustrated in FIG. 1B, so that the first rod 100 has a shape extending along the TK of an anatomically normal spinal column arrangement. Note that the straight section 102 may include a slight curve. The rod length L10 of the first rod 100 includes five variations; 200 to 230 mm, 230 to 260 mm, 260 to 290 mm, 290 to 320 mm, and 320 to 350 mm. The rod length L10 is a length that connects both ends of the first rod 100 along the central line thereof. The radiuses of the curvatures of the curved sections 101, 103 are preferably 180 mm to 430 mm, inclusive. The length L11 of the straight section 102 is preferably one quarter to one half the rod length L10, inclusive. The length L12 of the reverse curved section 104 is preferably a tenth to a fifth of the rod length L10, inclusive. The radius of the curvature of the reverse curved section 104 is preferably 110 mm to 220 mm, inclusive. In this way, an anatomically normal spinal column arrangement can be acquired in spinal deformity correction and fusion. These values have been obtained from clinical data as will be described later. The first rod radius D1 of the first rod 100 is preferably 4 to 6 mm. The first rod 100 is molded by laminating titanium alloy powders or cobalt chromium alloy powders by electron beam layered manufacturing, and the laminate-molded laminate body is heat treated to eliminate the residual stress in the laminated direction.

The second rod 200 has, as illustrated in FIG. 1C, a first curved section 201 to be attached to the thoracic vertebrae and a second curved section 202 to be attached to the lumbar vertebrae. The first curved section 201 and the second curved section 202 are connected at an inflection point 1. The first curved section 201 has a shape extending along the TK of an anatomically normal spinal column arrangement. The second curved section 202 has a shape that curves in an opposite direction to the first curved section 201 and extends along the lumbar lordosis of an anatomically normal spinal column arrangement. The rod length L20 of the second rod 200 includes six variations; 230 to 260 mm, 260 to 290 mm, 290 to 320 mm, 320 to 350 mm, 350 to 380 mm, and 380 to 410 mm. The rod length L20 is a length that connects both ends of the second rod 200 along the central line thereof. The radius of the curvature of the first curved section 201 of the second rod 200 is preferably less than or equal to 280 mm, and the radius of the curvature of the second curved section 202 is preferably less than or equal to 280 mm. The length L21 of the first curved section 201 is preferably one half to two-thirds of the rod length L20, inclusive. In this way, an anatomically normal spinal column arrangement can be acquired in spinal deformity correction and fusion. These values have been obtained based on clinical data as will be described later. The second rod radius D2 of the second rod 200 is preferably 4 to 6 mm. In the same way as the first rod 100, the second rod 200 is molded by laminating titanium alloy powders or cobalt chromium alloy powders by electron beam layered manufacturing, and the laminate-molded laminate body is heat treated to eliminate the residual stress in the laminated direction.

Figure 2:
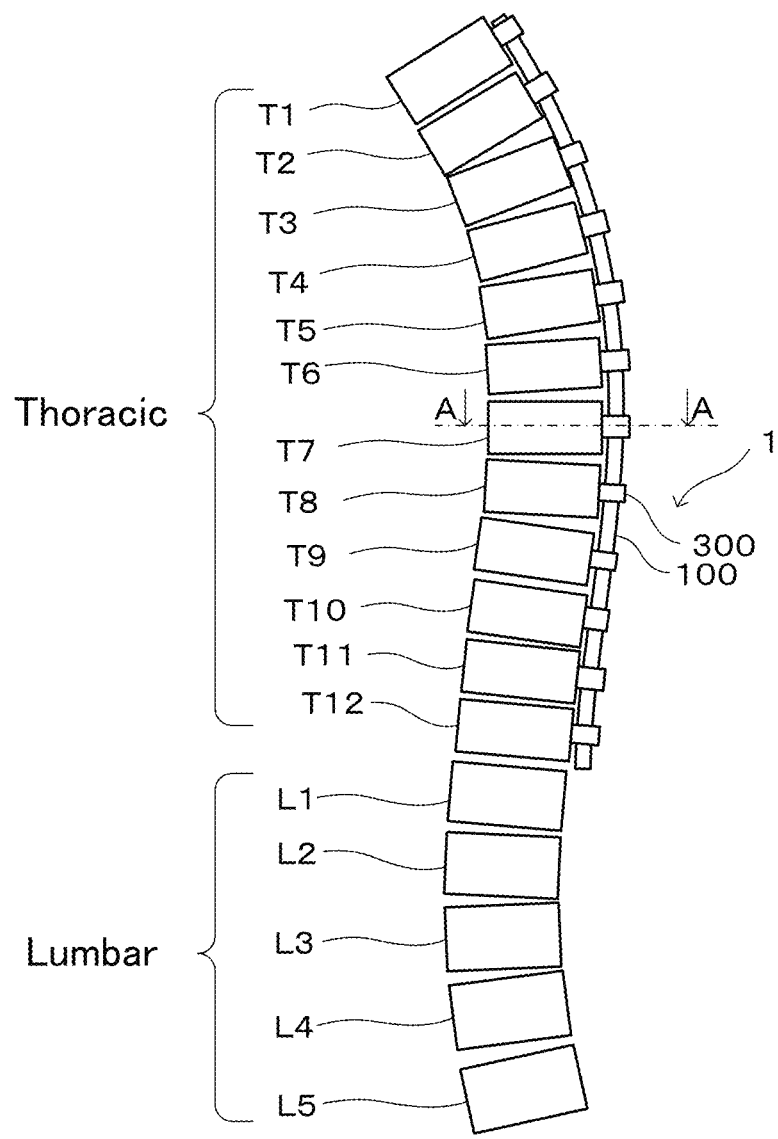
FIG. 2 is a diagram illustrating a state where the first rod is used in spinal deformity correction and fusion and is attached to the spinal column according to the embodiment of the present disclosure.
Figure 4:
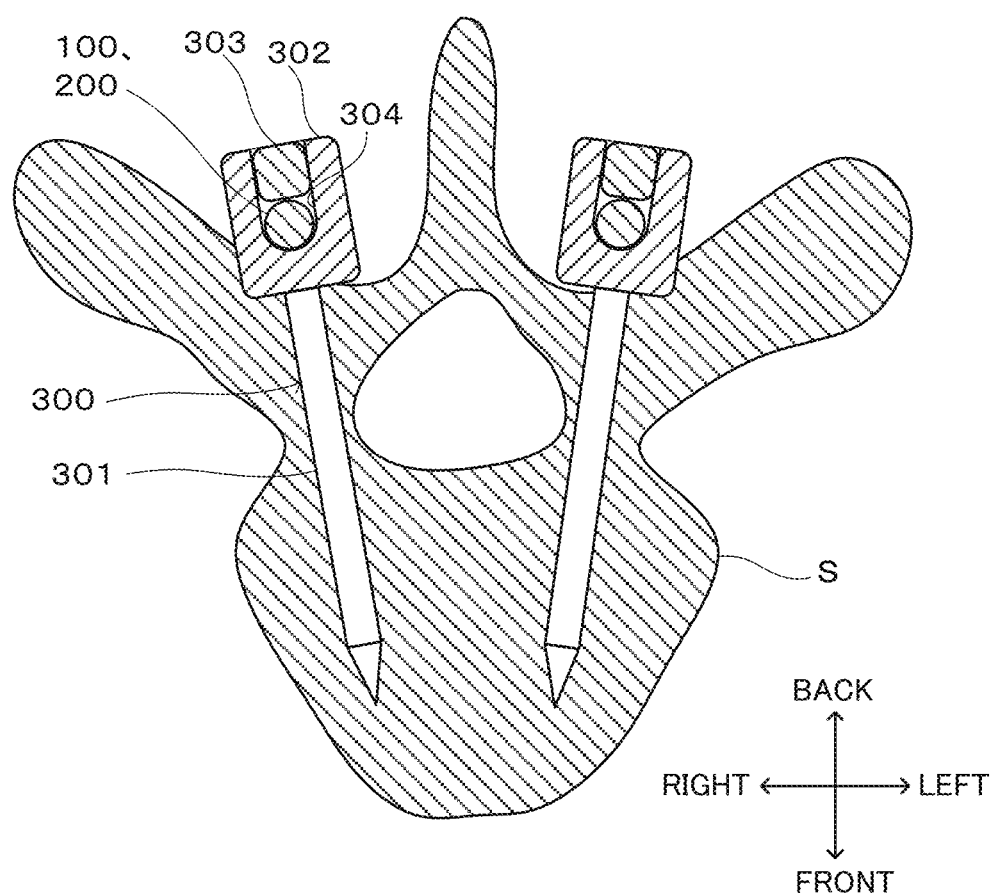
FIG. 4 is a section view taken along A-A of FIG. 2.

The first rod 100 is used, for example, as illustrated in FIG. 2, by being attached to a portion of the spinal column of a patient including the twelve thoracic vertebrae T1 to T12 with pedicle screws 300. The second rod 200 is used, for example, as illustrated in FIG. 3, by being attached to a portion of the spinal column of a patient including the twelve thoracic vertebrae T1 to T12 and the five lumbar vertebrae L1 to L5 with pedicle screws 300. In particular, as illustrated in FIG. 4, a single rod (the first rod 100 or the second rod 200) is attached to each of the left side and right side of the spinal column with the pedicle screws 300. The pedicle screw 300 includes a bone-screw part 301, a tulip shaped head 302, and a securing screw 303. The tulip shaped head 302 is attached to the bone-screw part 301 in a manner movable with respect to multiple axes and has a receptacle 304 that receives the second rod 200. The securing screw 303 secures the second rod 200 to the tulip shaped head 302. The second rod 200 used on the left side of the spinal column and the second rod 200 used on the right side of the spinal column are the same sizes and shapes.

Figure 5:
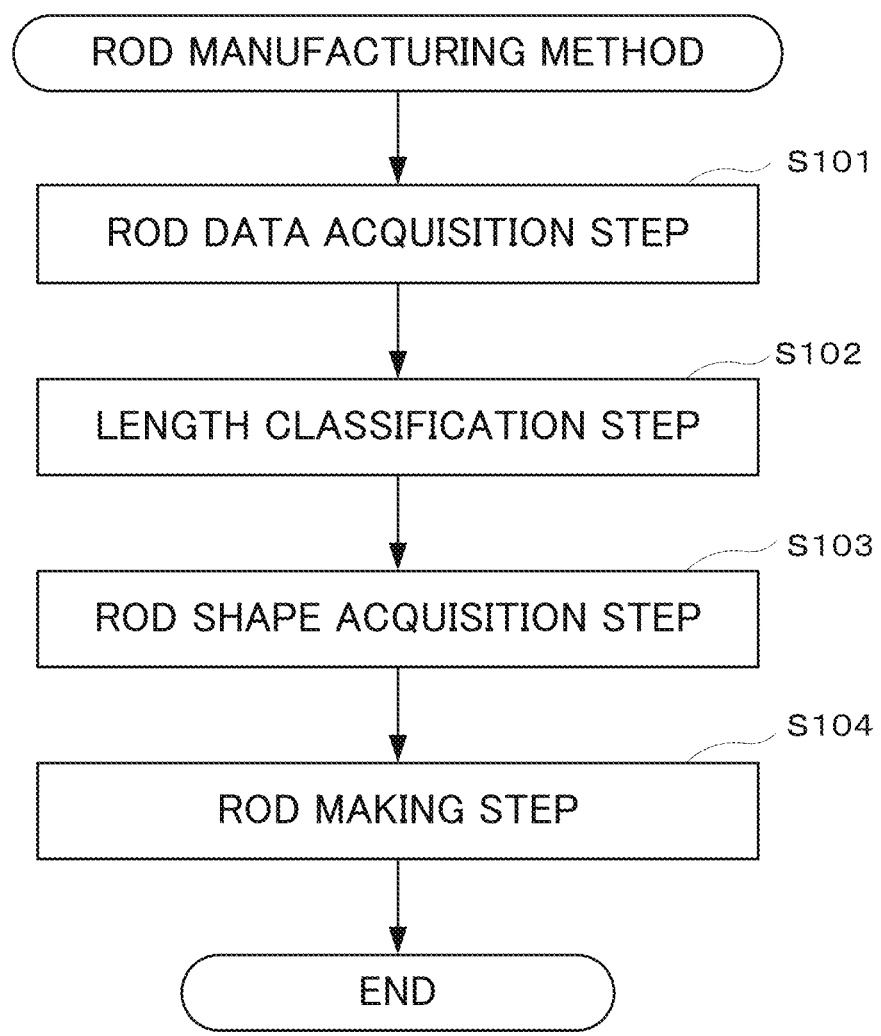
FIG. 5 is a flowchart illustrating a rod manufacturing method according to the embodiment of the present disclosure.

The following will describe a manufacturing method of the first rod 100 and the second rod 200. The manufacturing method of the first rod 100 and the second rod 200 includes: as illustrated in FIG. 5, a rod data acquisition step of acquiring data indicating a plurality of rod shapes that were bent in shapes extending along anatomically normal spinal column arrangements (step S101) a length classification step of classifying data indicating the rod shapes obtained at the rod data acquisition step (step S101) into groups of rod lengths with a difference of reference length (step S102); a rod shape acquisition step of acquiring data indicating best-fit curves from the rod shapes included in the groups classified at the length classification step (step S102)(step S103); a rod making step of making rods, based on the best-fit curves obtained at the rod shape acquisition step (step S103)(step S104). The rod data acquisition step (step S101), the length classification step (step S102), and the rod shape acquisition step (step S103) are executed by a computer that has a central processing unit (CPU) and a storage unit.

First, anatomically normal spinal column arrangements without thoracic idiopathic scoliosis were predicted for patients with thoracic idiopathic scoliosis. Rods were bent into shapes extending along the predicted spinal column arrangements.

Next, the rod data acquisition step (step S101) was performed. Specifically, two-dimensional (2D) computer-aided design (CAD) data were obtained by tracing the shapes of left side rods before implanting them into the bodies of 47 patients who underwent posterior spinal correction and fusion using the bent rods. The obtained 2D-CAD data indicating the left side rod shapes were stored in the storage unit of the computer. Note that, anatomically normal spinal column arrangements were obtained for the 47 patients who underwent the posterior spinal correction and fusion. Rod central curves were extracted from the 2D-CAD data stored in the storage unit, and shape difference value evaluation was performed among the central curves by an iterative closest point (OCP) method.

Next, at the length classification step (step S102), the data were classified into seven groups with a difference of reference length of 30 mm, based on the rod lengths before bending processing (200 to 410 mm). Although the reference length was 30 mm in this example, the reference length may change as necessary, for example, the reference length may be 20 mm, 25 mm, 40 mm, or 50 mm.

At the rod shape acquisition step (step S103), hierarchical cluster analysis was performed on a central curve group in each of the seven groups, and a best-fit curve with the smallest difference value with reference to a rod of the maximum length in each cluster was calculated. The average straight rod length before bending processing was 279 mm, and all combinations of the rod central curves after bending processing obtained by the ICP method were 1018 patterns. By the hierarchical cluster analysis on the central curve groups of respective lengths, a total of eleven kinds of best-fit curves were calculated with the maximum difference value within 5 mm. In this way, 2D-CAD data of a best-fit curve group that can be used for rods were obtained.

At the rod making step (step S104), using three-dimensional shape data obtained by combining the 2D-CAD data that indicate the best-fit curves, the first rod length L10, the second rod length L20, the first rod diameter D1, and the second rod diameter D2, the first rod 100 and the second rod 200 were manufactured by laminating titanium alloy powders or cobalt chromium alloy powders by an electron beam layered manufacturing method to form a laminate body and heat processing the laminate body so as to eliminate residual stress in the laminated direction.

The following will further describe an algorithm of generating a best-fit curve in more detail with an example of the first rod 100 with the rod length L10 in a range from 200 to 230 mm.

Figure 6:
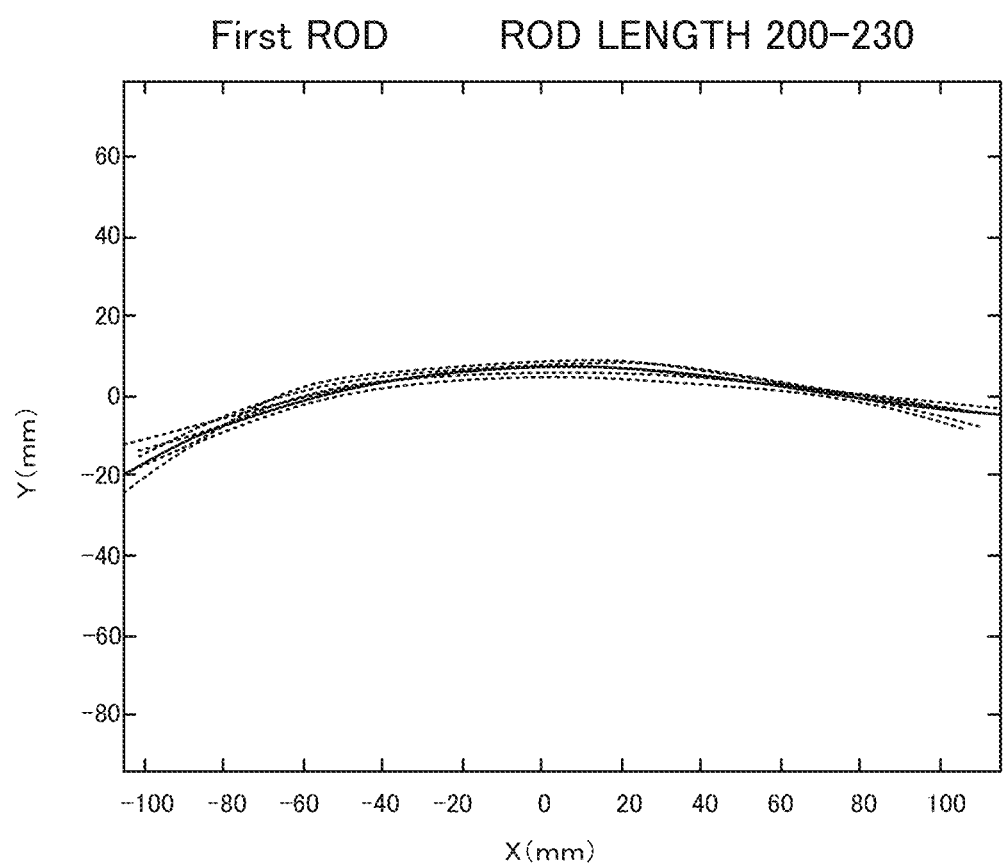
FIG. 6 is a diagram illustrating a set of data points and a best-fit curve for a first rod with a rod length of 200 to 230 mm according to the embodiment of the present disclosure.

First, at the length classification step (step S102), based on the 21-CAD data of the left-side rod shapes that were traced before implanting the rods into the bodies, 20-CAD data with the rod length L10 of 200 to 230 mm that are classified into a cluster of the first rod 100 are extracted. Next, rod central curve data are extracted from the 21-CAD data. Next, at the rod shape acquisition step (step S103), as illustrated in FIG. 6, sampling point groups on rod central curves are generated. The curve with the longest rod central curve length within the cluster is selected as a reference curve. Next, the sampling point groups of curves other than those of the reference curve are aligned by ICP with reference to the sampling point group of the reference curve, and a point group after alignment is generated. A set of data points (a dot line portion illustrated in FIG. 6) are generated by combining the sampling point group of the reference curve and the point group after alignment of the curves other than the reference curve. A best-fit curve, with which the sum of the squares of the fit error for the set of data points is minimized, is calculated as "least-squares uniform B-spline curve of degree 6" (a solid line portion illustrated in FIG. 6) by a function spap2( ) of Matlab (registered trademark) Curve fitting toolbox (trademark) of MathWorks, Inc. A polygon shape that discretely approximates the sweep surface of the best-fit curve as a central axis having a circle cross section with a diameter of 5.5 mm is generated, and the polygon shape is output in a standard template library (STL) file format from the Matlab. (The number of straight divisions around a central axis/in a circumferential direction can be specified in the program. Three-hundred divisions around the central axis direction and 72 divisions in the circumferential direction may preferably be set.) Although an example of obtaining a best-fit curve from 2D-CAD data of left-side rod shapes has been described, it is understood that the best-fit curve obtained from the 2D-CAD data of the left-side rod shapes can be applied to a right-side rod since the sizes and shapes of the left-side rod and the right-side rod are the same.

Figure 7:
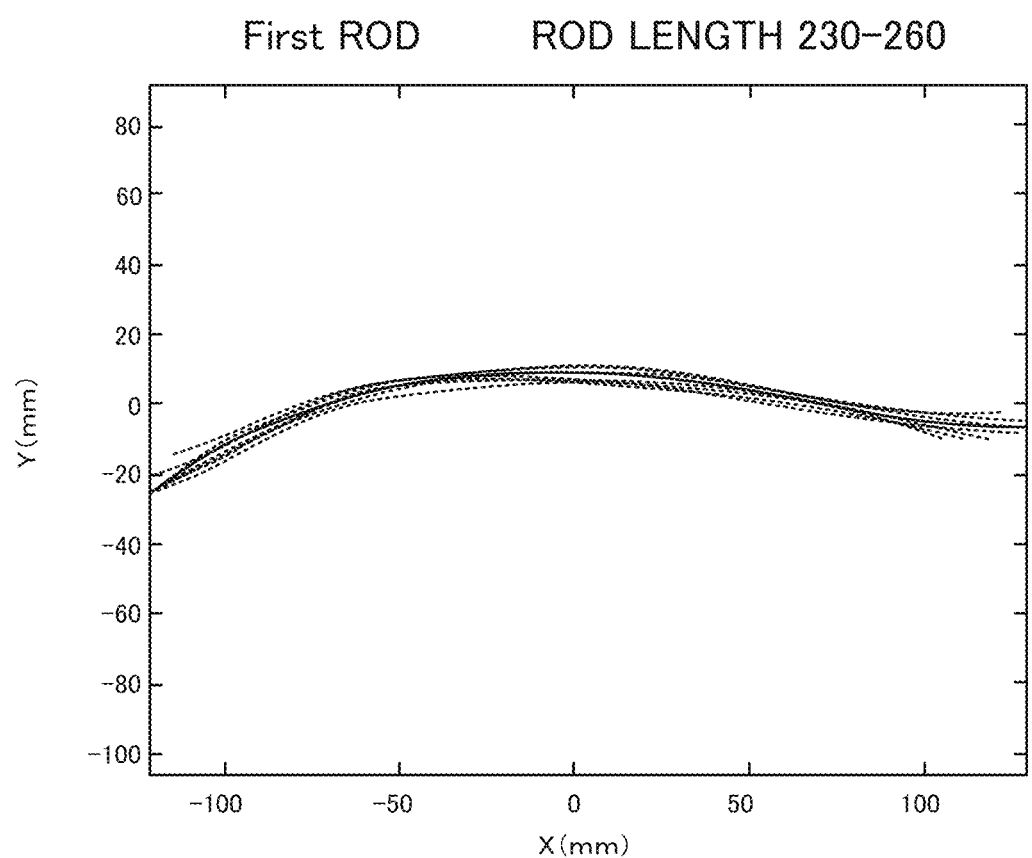
FIG. 7 is a diagram illustrating a set of data points and a best-fit curve for a first rod with a rod length of 230 to 260 mm according to the embodiment of the present disclosure.
Figure 8:
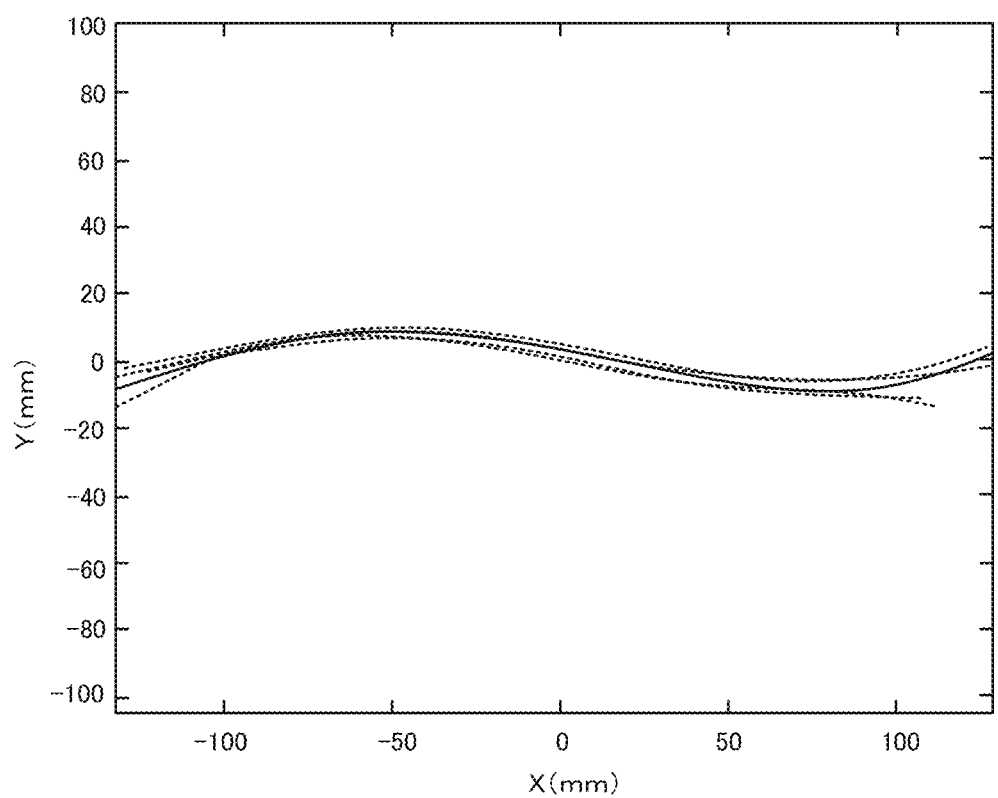
FIG. 8 is a diagram illustrating a set of data points and a best-fit curve for a second rod with a rod length of 230 to 260 mm according to the embodiment of the present disclosure.
Figure 9:
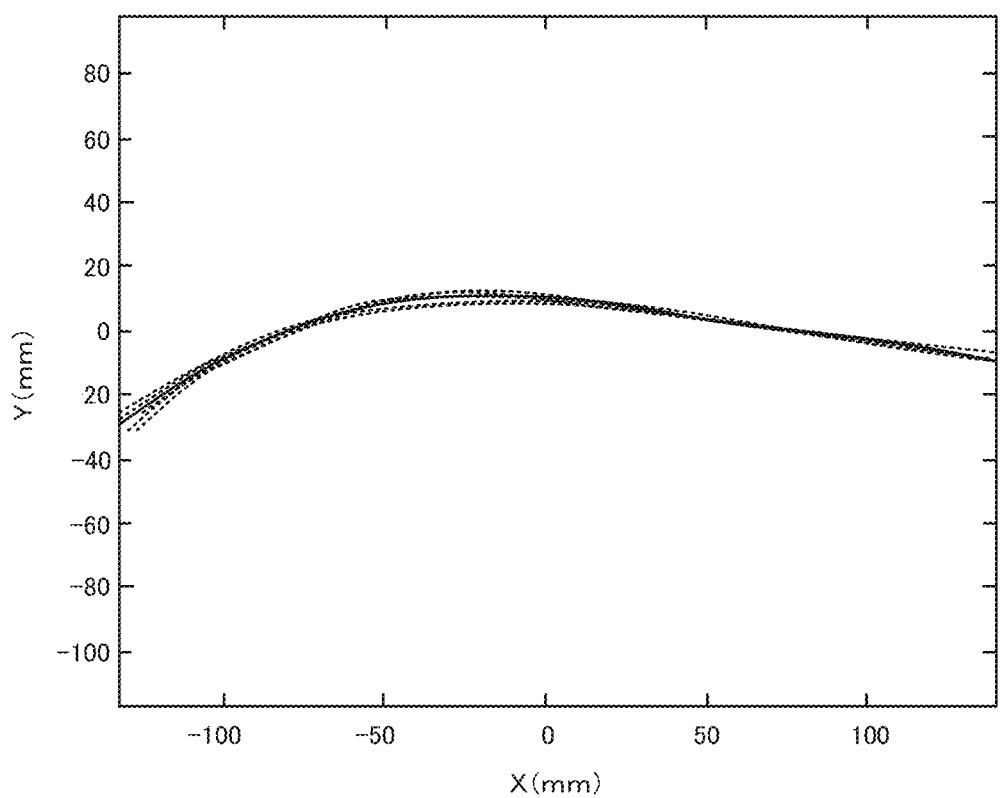
FIG. 9 is a diagram illustrating a set of data points and a best-fit curve for a first rod with a rod length of 260 to 290 mm according to the embodiment of the present disclosure.
Figure 10:
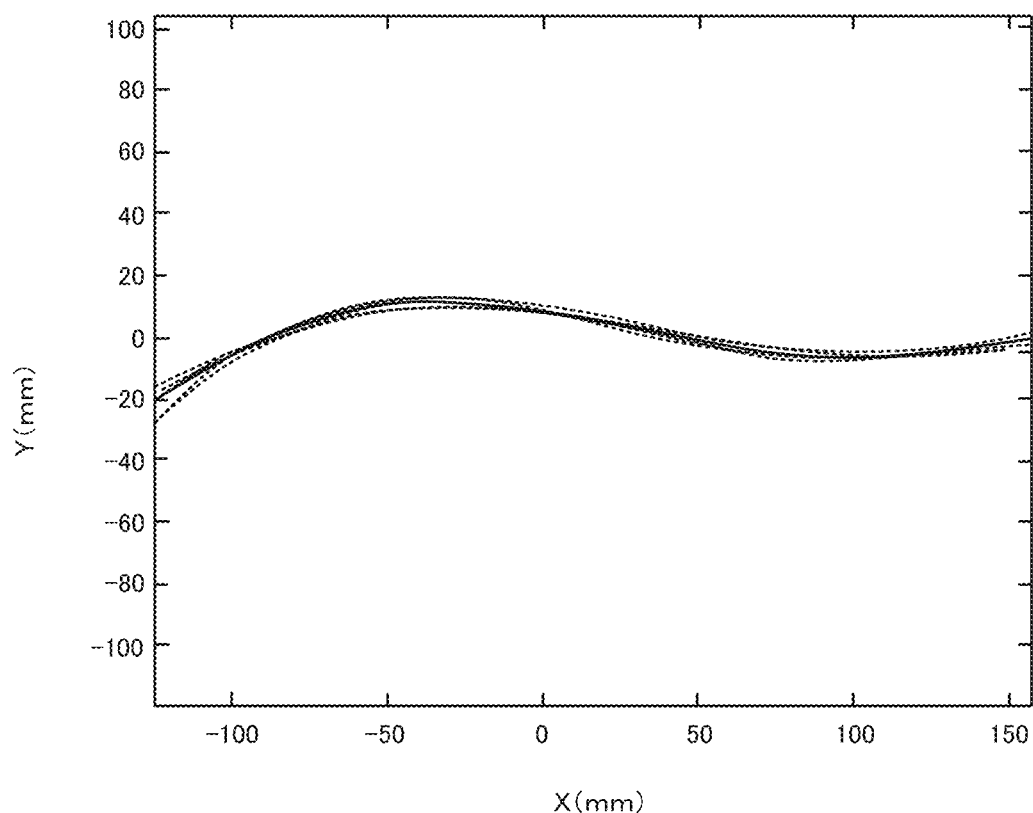
FIG. 10 is a diagram illustrating a set of data points and a best-fit curve for a second rod with a rod length of 260 to 290 mm according to the embodiment of the present disclosure.
Figure 11:
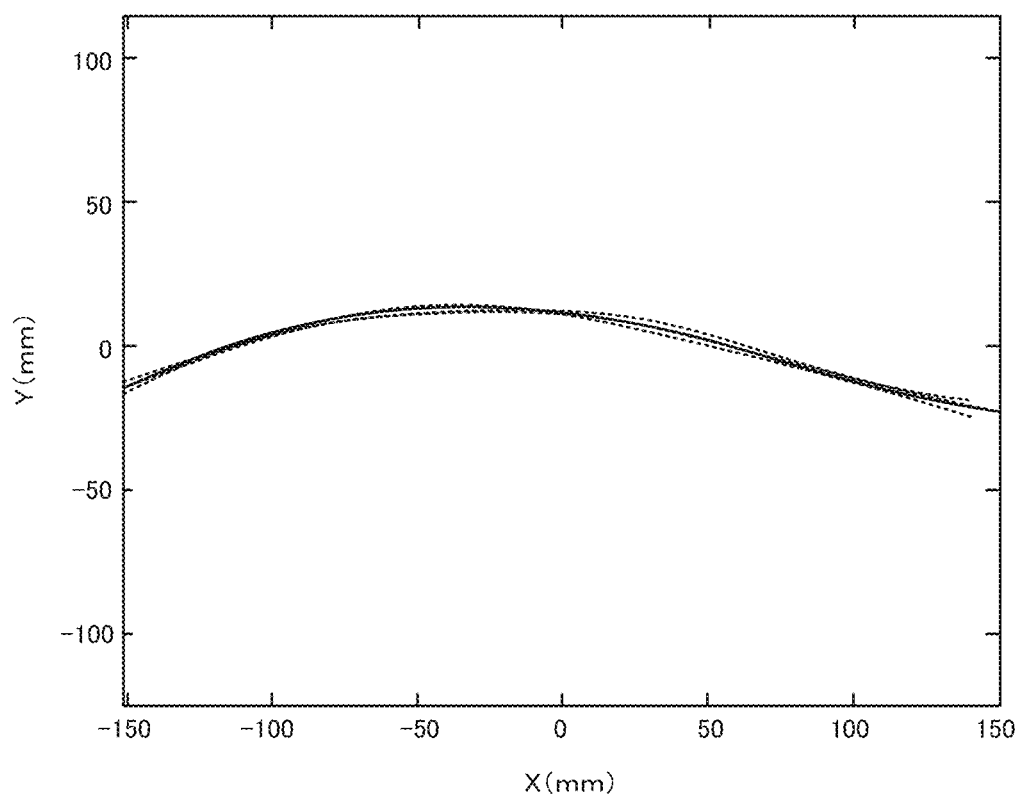
FIG. 11 is a diagram illustrating a set of data points and a best-fit curve for a first rod with a rod length of 290 to 320 mm according to the embodiment of the present disclosure.
Figure 12:
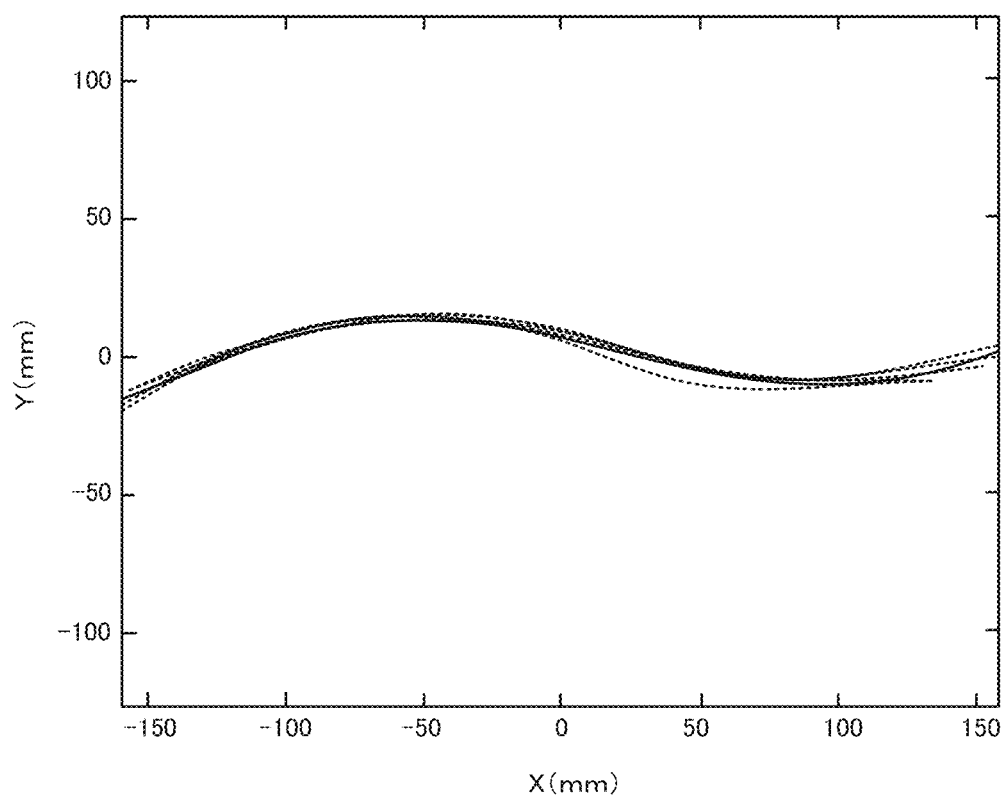
FIG. 12 is a diagram illustrating a set of data points and a best-fit curve for a second rod with a rod length of 290 to 320 mm according to the embodiment of the present disclosure.
Figure 13:
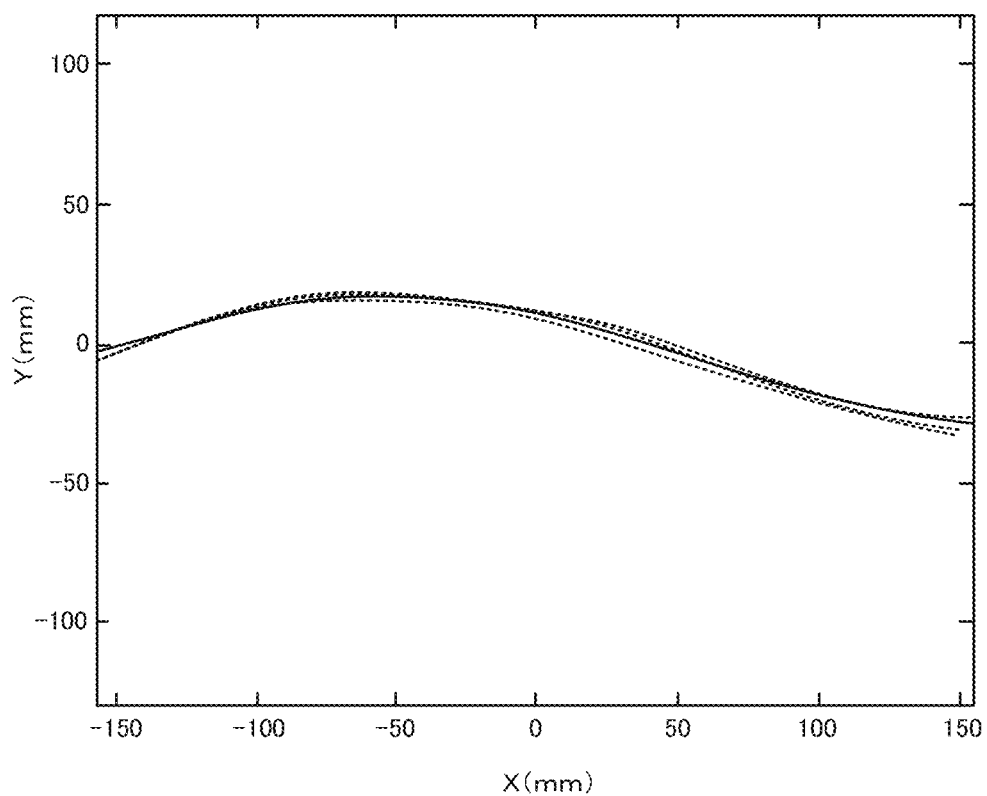
FIG. 13 is a diagram illustrating a set of data points and a best-fit curve for a first rod with a rod length of 320 to 350 mm according to the embodiment of the present disclosure.
Figure 14:
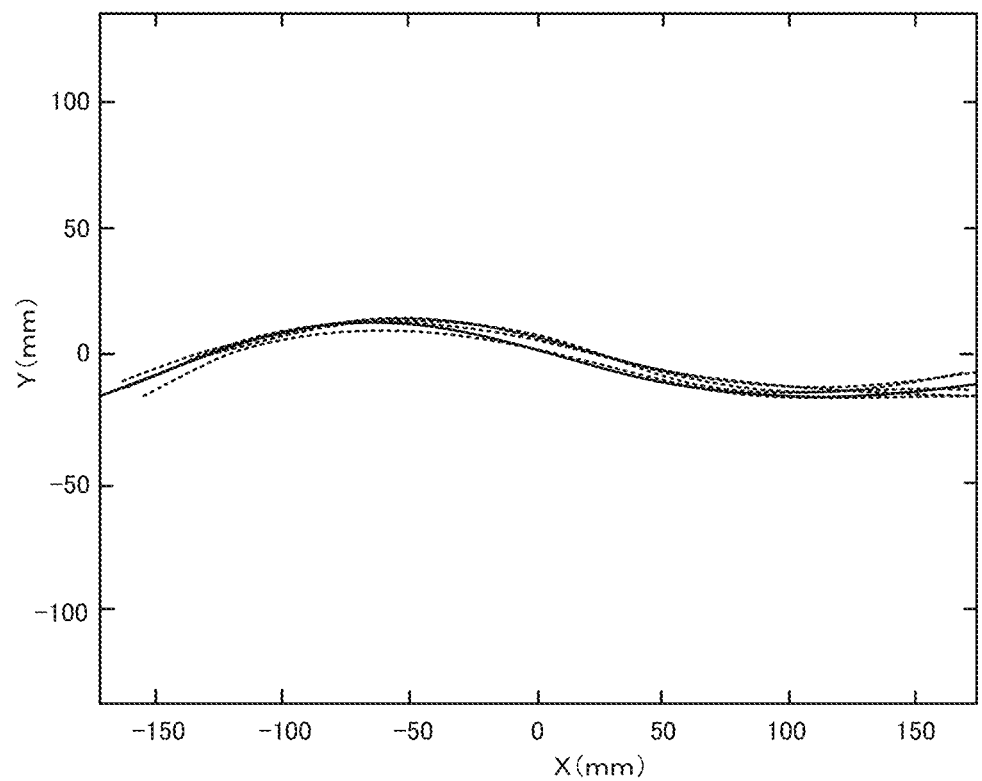
FIG. 14 is a diagram illustrating a set of data points and a best-fit curve for a second rod with a rod length of 320 to 350 mm according to the embodiment of the present disclosure.
Figure 15:
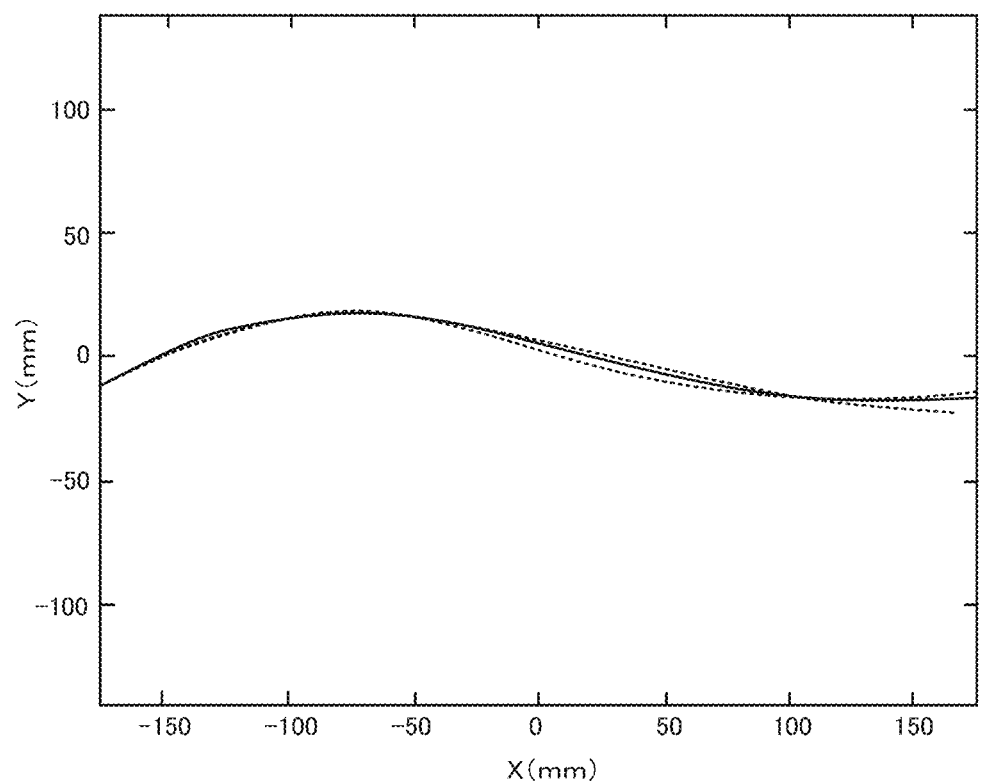
FIG. 15 is a diagram illustrating a set of data points and a best-fit curve for a second rod with a rod length of 350 to 380 mm according to the embodiment of the present disclosure.
Figure 16:
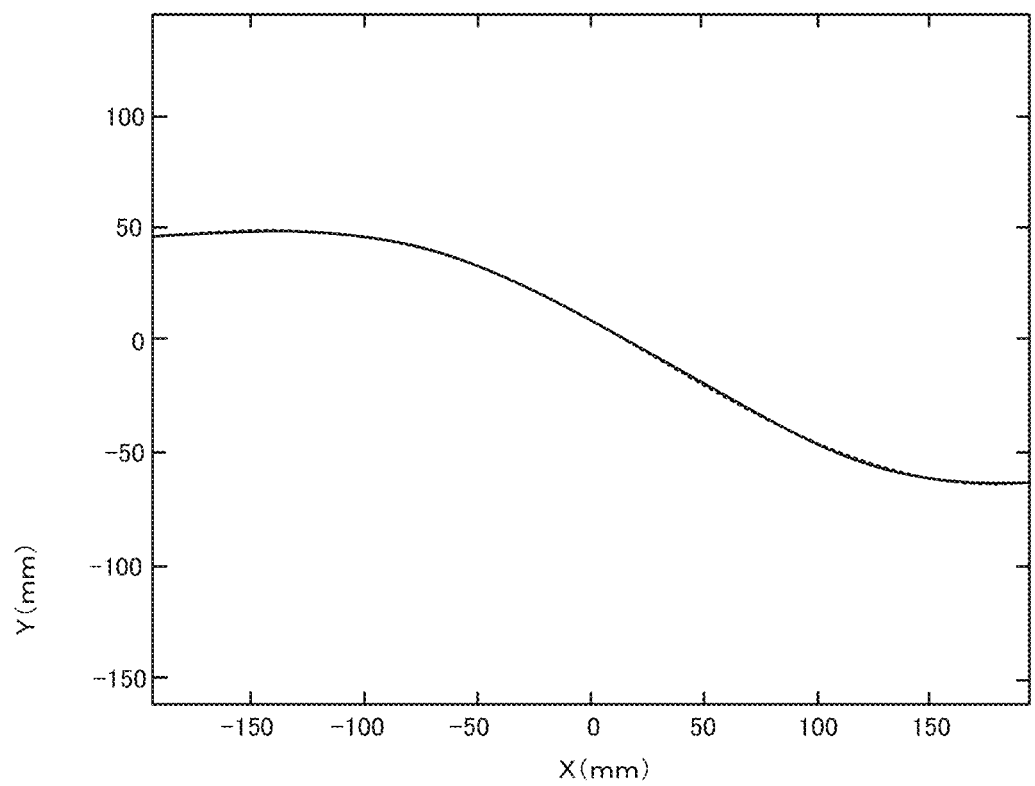
FIG. 16 is a diagram illustrating a set of data points and a best-fit curve for a second rod with a rod length of 380 to 410 mm according to the embodiment of the present disclosure.

Likewise, as for a cluster of the first rod 100 with the rod length L10 in a range of 230 to 260 mm, as illustrated in FIG. 7, a best-fit curve illustrated by a solid line can be obtained from the set of data points illustrated by dot lines. As for a cluster of the second rod 200 with the rod length L20 in a range of 230 to 260 mm, as illustrated in FIG. 8, a best-fit curve illustrated by a solid line can be obtained from the set of data points illustrated by dot lines. As fora cluster of the first rod 100 with the rod length L10 in a range of 260 to 290 mm, as illustrated in FIG. 9, a best-fit curve illustrated by a solid line can be obtained from the set of data points illustrated by dot lines. As for a cluster of the second rod 200 with the rod length L20 in a range of 260 to 290 mm, as illustrated in FIG. 10, a best-fit curve illustrated by a solid line can be obtained from the set of data points illustrated by dot lines. As for a cluster of the first rod 100 with the rod length L10 in a range of 290 to 320 mm, as illustrated in FIG. 11, a best-fit curve illustrated by a solid line can be obtained from the set of data points illustrated by dot lines. As for a cluster of the second rod 200 with the rod length L20 in a range of 290 to 320 mm, as illustrated in FIG. 12, a best-fit curve illustrated by a solid line can be obtained from the set of data points illustrated by dot lines. As for a cluster of the first rod 100 with the rod length L10 in a range of 320 to 350 mm, as illustrated in FIG. 13, a best-fit curve illustrated by a solid line can be obtained from the set of data points illustrated by dot lines. As for a cluster of the second rod 200 with the rod length L20 in a range of 320 to 350 mm, as illustrated in FIG. 14, a best-fit curve illustrated by a solid line can be obtained from the set of data points illustrated by dot lines. As for a cluster of the second rod 200 with the rod length L20 in a range of 350 to 380 mm, as illustrated in FIG. 15, a best-fit curve illustrated by a solid line can be obtained from the set of data points illustrated by dot lines. As for a cluster of the second rod 200 with the rod length L20 in a range of 380 to 410 mm, as illustrated in FIG. 16, a best-fit curve illustrated by a solid line can be obtained from the set of data points illustrated by dot lines.

Figure 17:
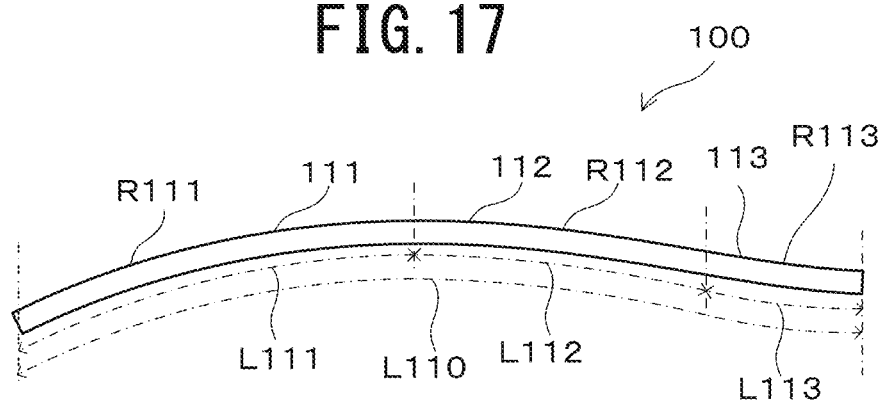
FIG. 17 is a diagram illustrating the first rod with the rod length of 200 to 230 mm according to the embodiment of the present disclosure.

The first rod 100 with the rod length L10 in the range of 200 to 230 mm, which has been obtained from the best-fit curve obtained as described above, has sections 111 to 113 that are continuously connected as illustrated in FIG. 17. The full length of the first rod 100 is L110=225 mm; the length of the section 111 is L111=106 mm; the length of the section 112 is L112=77 mm; the length of the section 113 is L113=42 mm; the radius of the curvature of the section 111 is R111=236 mm; the radius of the curvature of the section 112 is R112=376 mm; and the radius of the curvature of the section 113 is R113=218 mm. The section 111 and the section 112 are curved in the same direction and the section 113 is curved in an opposite direction to the section 111 and the section 112. The section 113 constitutes the reverse curved section 104.

Figure 18:
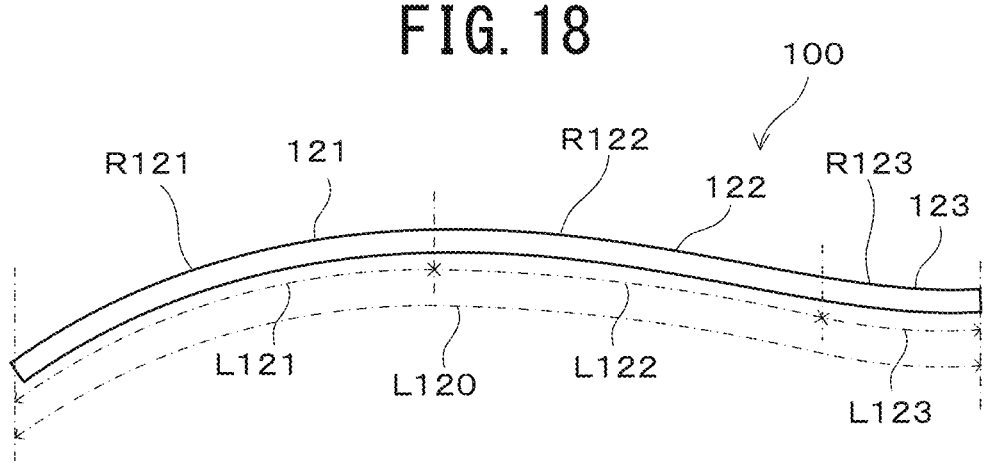
FIG. 18 is a diagram illustrating the first rod with the rod length of 230 to 260 mm according to the embodiment of the present disclosure.

The first rod 100 with the rod length L10 in the range of 230 to 260 mm has sections 121 to 123 that are continuously connected as illustrated in FIG. 18. The full length of the first rod 100 is L120=259 mm; the length of the section 121 is L121=116 mm; the length of the section 122 is L122=102 mm; the length of the section 123 is L123=41 mm; the radius of the curvature of the section 121 is R121=194 mm; the radius of the curvature of the section 122 is R122=428 mm; and the radius of the curvature of the section 123 is R123=118 mm. The section 121 and the section 122 are curved in the same direction and the section 123 is curved in an opposite direction to the section 121 and the section 122. The section 123 constitutes the reverse curved section 104.

Figure 19:
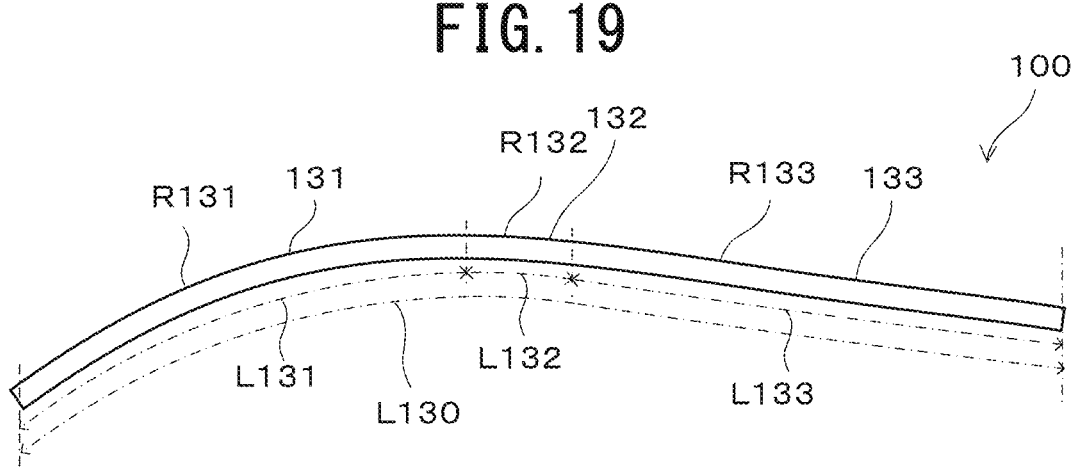
FIG. 19 is a diagram illustrating the first rod with the rod length of 260 to 290 mm according to the embodiment of the present disclosure.

The first rod 100 with the rod length L10 in the range of 260 to 290 mm has sections 131 to 133 that are continuously connected as illustrated in FIG. 19. The full length of the first rod 100 is L130=285 mm; the length of the section 131 is L131=126 mm; the length of the section 132 is L132=29 mm; the length of the section 133 is L133=130 mm; the radius of the curvature of the section 131 is R131=183 mm; the radius of the curvature of the section 132 is R132=201 mm; and the radius of the curvature of the section 133 is R133=7543 mm. The section 131 and the section 132 are curved in the same direction and the section 133 is curved in an opposite direction to the section 131 and the section 132. The section 133 constitutes the straight section 102.

Figure 20:
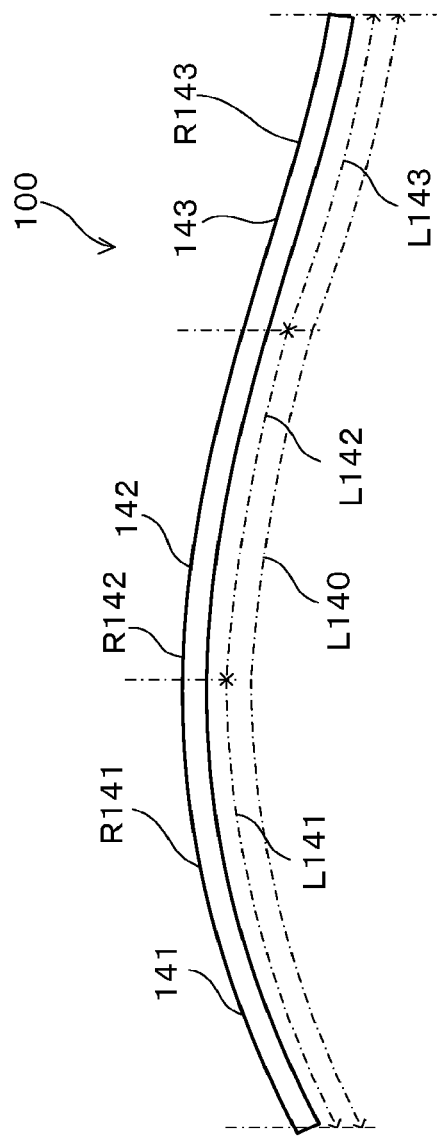
FIG. 20 is a diagram illustrating the first rod with the rod length of 290 to 320 mm according to the embodiment of the present disclosure.

The first rod 100 with the rod length L10 in the range of 290 to 320 mm has sections 141 to 143 that are continuously connected as illustrated in FIG. 20. The full length of the first rod 100 is L140=313 mm; the length of the section 141 is L141=126 mm; the length of the section 142 is L142=97 mm; the length of the section 143 is L143=90 mm; the radius of the curvature of the section 141 is R141=266 mm; the radius of the curvature of the section 142 is R142=309 mm; and the radius of the curvature of the section 143 is R143=700 mm. The section 141 and the section 142 are curved in the same direction and the section 143 is curved in an opposite direction to the section 141 and the section 142. The section 143 constitutes the straight section 102.

Figure 21:
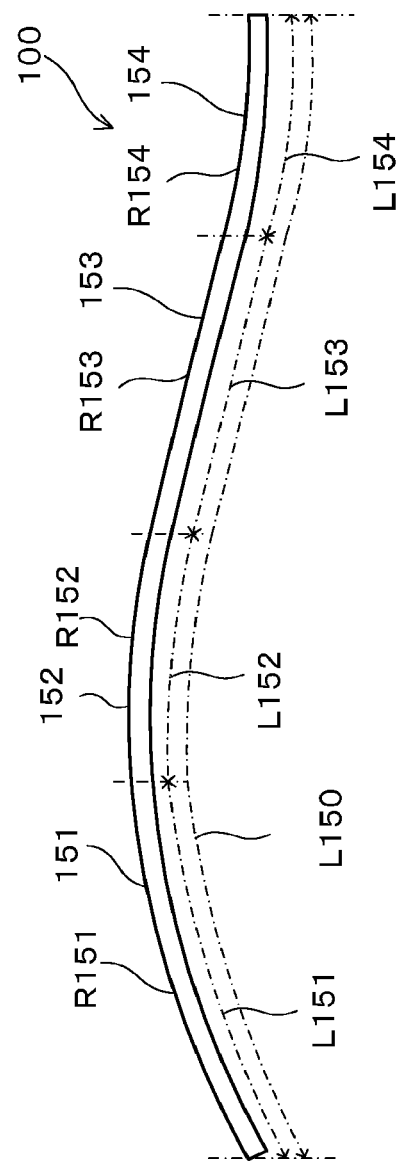
FIG. 21 is a diagram illustrating the first rod with the rod length of 320 to 350 mm according to the embodiment of the present disclosure.

The first rod 100 with the rod length L10 in the range of 320 to 350 mm has sections 151 to 154 that are continuously connected as illustrated in FIG. 21. The full length of the first rod 100 is L150=329 mm; the length of the section 151 is L151=110 mm; the length of the section 152 is L152=70 mm; the length of the section 153 is L153=86 mm; the length of the section 154 is L154=63 mm; the radius of the curvature of the section 151 is R151=274 mm; the radius of the curvature of the section 152 is R152=250 mm; the radius of the curvature of the section 153 is R153=2361 mm; and the radius of the curvature of the section 154 is R154=217 mm. The sections 151 to 153 are curved in the same direction and the section 154 is curved in an opposite direction to the sections 151 to 153. The section 154 constitutes the reverse curved section 104.

Figure 22:
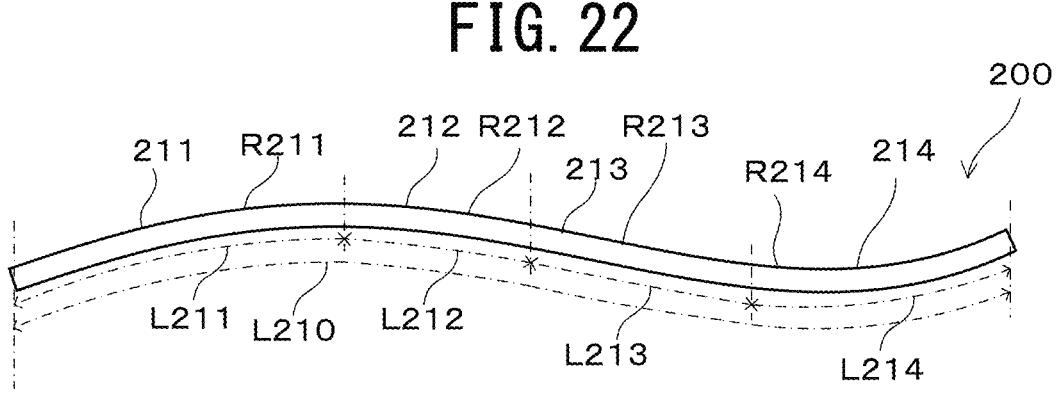
FIG. 22 is a diagram illustrating the second rod with the rod length of 230 to 260 mm according to the embodiment of the present disclosure.

The second rod 200 with the rod length L20 in the range of 230 to 260 mm has sections 211 to 214 that are continuously connected as illustrated in FIG. 22. The full length of the second rod 200 is L210=264 nm; the length of the section 211 is L211=77 mm; the length of the section 212 is L212=64 mm; the length of the section 213 is L213=57 mm; the length of the section 214 is L214=66 mm; the radius of the curvature of the section 211 is R211=160 mm; the radius of the curvature of the section 212 is R212=311 mm; the radius of the curvature of the section 213 is R213=570 mm; and the radius of the curvature of the section 214 is R214=140 mm. The section 211 and the section 212 are curved in the same direction, and the section 213 and the section 214 are curved in an opposite direction to the section 211 and the section 212. The section 211 and the section 212 constitute the first curved section 201, and the section 213 and the section 214 constitute the second curved section 202.

Figure 23:
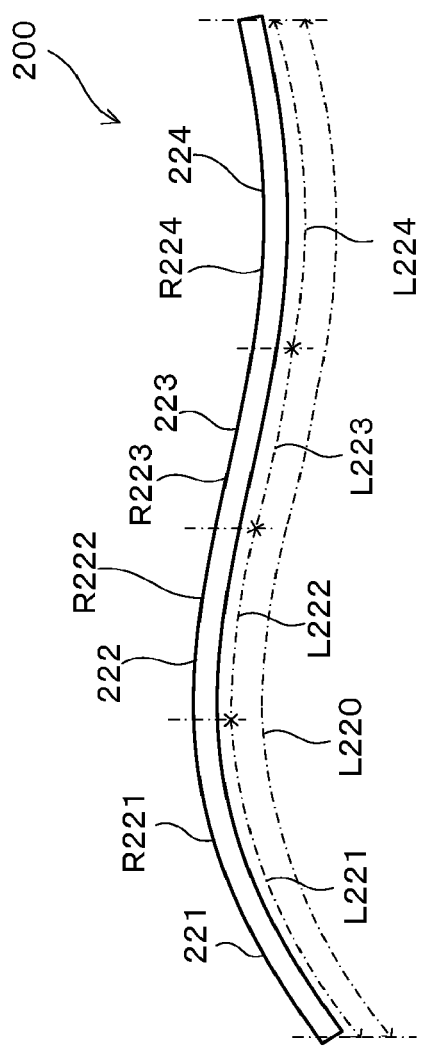
FIG. 23 is a diagram illustrating the second rod with the rod length of 260 to 290 mm according to the embodiment of the present disclosure.

The second rod 200 with the rod length L20 in the range of 260 to 290 mm has sections 221 to 224 that are continuously connected as illustrated in FIG. 23. The full length of the second rod 200 is L220=295 mm; the length of the section 221 is L221=101 mm; the length of the section 222 is L222=51 mm; the length of the section 223 is L223=39 mm; the length of the section 224 is L224=104 mm; the radius of the curvature of the section 221 is R221=147 mm; the radius of the curvature of the section 222 is R222=249 mm; the radius of the curvature of the section 223 is R223=3947 mm; and the radius of the curvature of the section 224 is R224=247 mm. The section 221 and the section 222 are curved in the same direction, and the section 223 and the section 224 are curved in an opposite direction to the section 221 and the section 222. The section 221 and the section 222 constitute the first curved section 201 and the section 223 and the section 224 constitute the second curved section 202.

Figure 24:
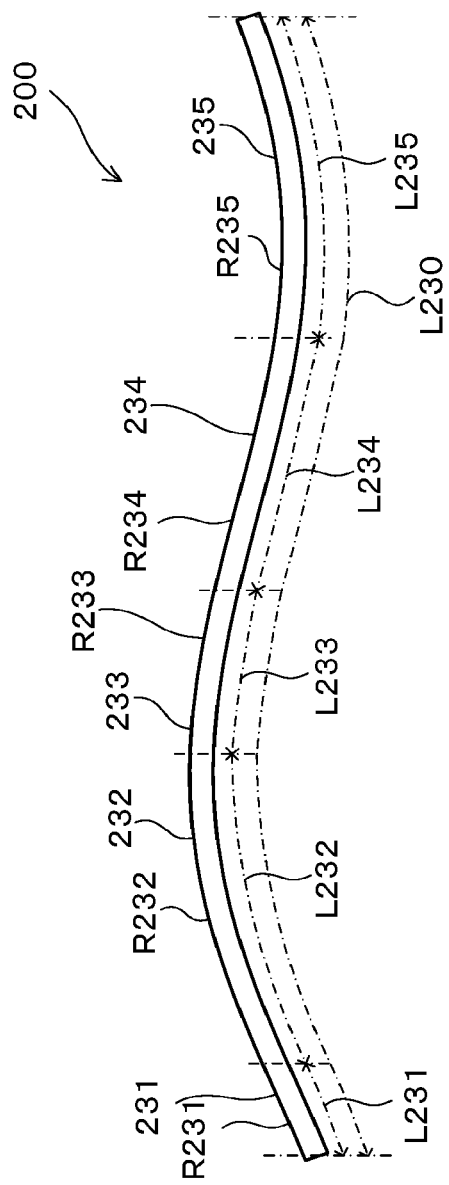
FIG. 24 is a diagram illustrating the second rod with the rod length of 290 to 320 mm according to the embodiment of the present disclosure.

The second rod 200 with the rod length L20 in the range of 290 to 320 mm has sections 231 to 235 that are continuously connected as illustrated in FIG. 24. The full length of the second rod 200 is L230=326 mm; the length of the section 231 is L231=28 mm; the length of the section 232 is L232=90 mm; the length of the section 233 is L233=45 mm; the length of the section 234 is L234=72 mm; the length of the section 235 is L235=91 mm; the radius of the curvature of the section 231 is R231=468 mm; the radius of the curvature of the section 232 is R232=219 mm; the radius of the curvature of the section 233 is R233=149 mm; the radius of the curvature of the section 234 is R234=510 mm; and the radius of the curvature of the section 235 is R235=173 mm. The section 232 and the section 233 are curved in the same direction, and the sections 231, 234, and 235 are curved in an opposite direction to the sections 232 and the section 233. The sections 231 to 233 constitute the first curved section 201, and the section 234 and the section 235 constitute the second curved section 202.

Figure 25:
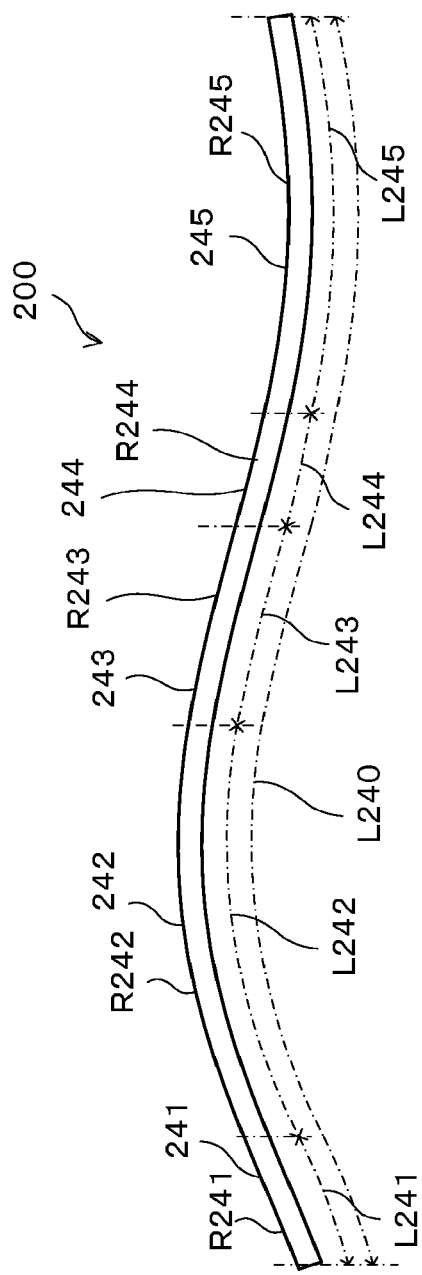
FIG. 25 is a diagram illustrating the second rod with the rod length of 320 to 350 mm according to the embodiment of the present disclosure.

The second rod 200 with the rod length L20 in the range of 320 to 350 mm has sections 241 to 245 that are continuously connected as illustrated in FIG. 25. The full length of the second rod 200 is L240)=354 mm; the length of the section 241 is L241=40 mm; the length of the section 242 is L242=115 mm; the length of the section 243 is L243=56 mm; the length of the section 244 is L244=32 mm; the length of the section 245 is L245=111 mm; the radius of the curvature of the section 241 is R241=497 mm; the radius of the curvature of the section 242 is R242=202 mm; the radius of the curvature of the section 243 is R243=497 mm; the radius of the curvature of the section 244 is R244=497 mm; and the radius of the curvature of the section 245 is R245=264 mm. The section 242 and the section 243 are curved in the same direction, and the sections 241, 244, and 245 are curved in an opposite direction to the sections 242 and the section 243. The sections 241 to 243 constitute the first curved section 201 and the section 244 and the section 245 constitute the second curved section 202.

Figure 26:
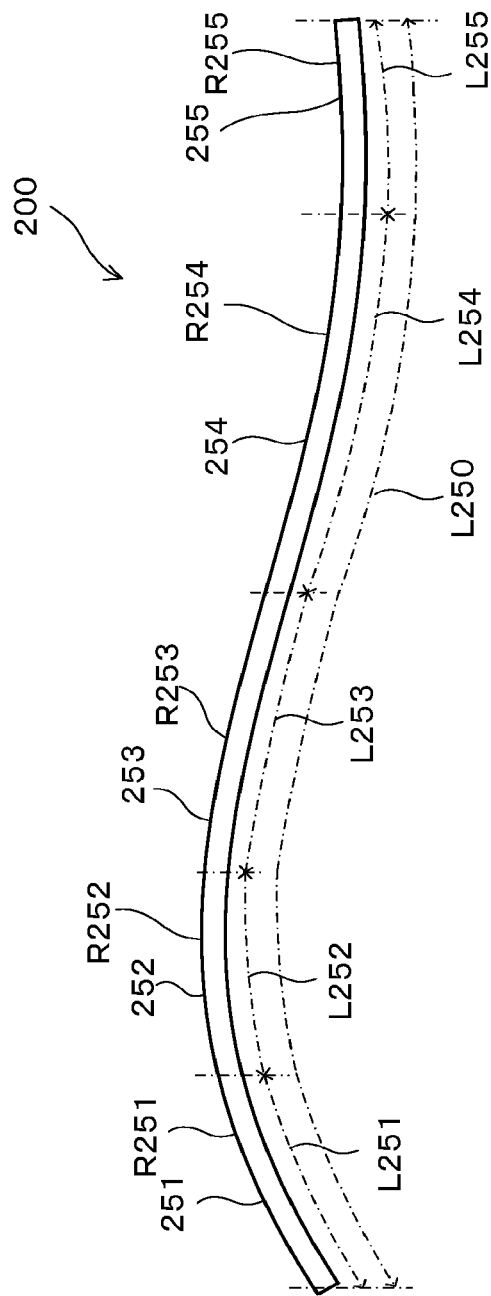
FIG. 26 is a diagram illustrating the second rod with the rod length of 350 to 380 mm according to the embodiment of the present disclosure.

The second rod 200 with the rod length L20 in the range of 350 to 380 mm has sections 251 to 255 that are continuously connected as illustrated in FIG. 26. The full length of the second rod 200 is L250=362 mm; the length of the section 251 is L251=66 mm; the length of the section 252 is L252=72 mm; the length of the section 253 is L253=63 mm; the length of the section 254 is L254=108 mm; the length of the section 255 is L255=53 mm; the radius of the curvature of the section 251 is R251=167 mm; the radius of the curvature of the section 252 is R252=203 mm; the radius of the curvature of the section 253 is R253=464 mm; the radius of the curvature of the section 254 is R254=482 mm; and the radius of the curvature of the section 255 is R255=279 mm. The sections 251 to 253 are curved in the same direction and the section 254 and the section 255 are curved in an opposite direction to the sections 251 to 253. The sections 251 to 253 constitute the first curved section 201, and the section 254 and the section 255 constitute the second curved section 202.

Figure 27:
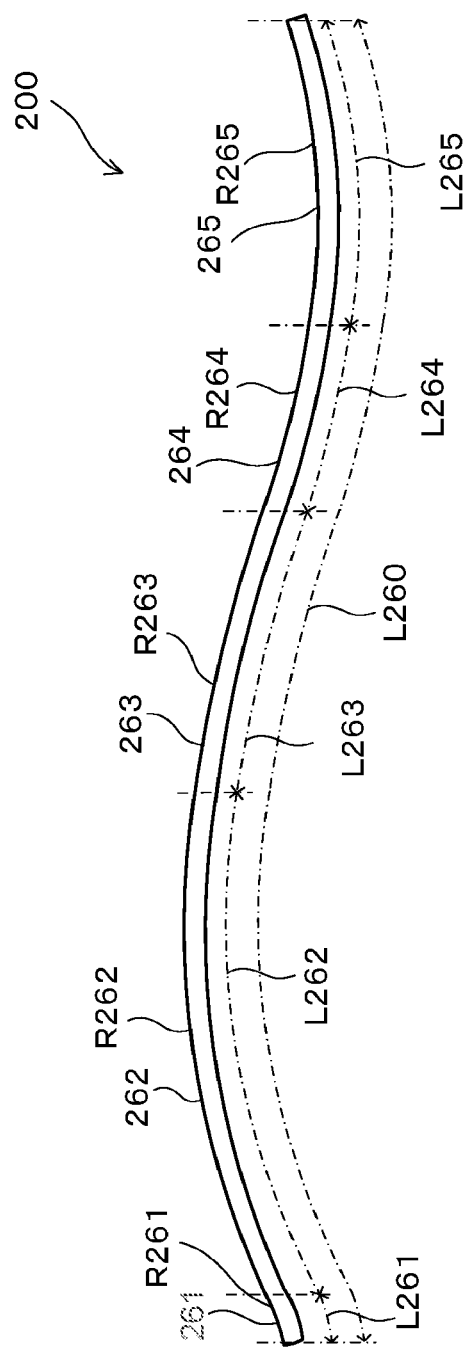
FIG. 27 is a diagram illustrating the second rod with the rod length of 380 to 410 mm according to the embodiment of the present disclosure.

The second rod 200 with the rod length L20 in the range of 380 to 410 mm has sections 261 to 265 that are continuously connected as illustrated in FIG. 27. The full length of the second rod 200 is L260=392 mm; the length of the section 261 is L261=16 mm; the length of the section 262 is L262=147 mm; the length of the section 263 is L263=83 mm; the length of the section 264 is L264=57 mm; the length of the section 265 is L265=89 mm; the radius of the curvature of the section 261 is R261=118 mm; the radius of the curvature of the section 262 is R262=271 mm; the radius of the curvature of the section 263 is R263=486 mm; the radius of the curvature of the section 264 is R264=351 mm; and the radius of the curvature of the section 265 is R265=204 mm. The section 262 and the section 263 are curved in the same direction, and the sections 261, 264, and 265 are curved in an opposite direction to the sections 262 and the section 263. The sections 261 to 263 constitute the first curved section 201, and the sections 264 and the section 265 constitute the second curved section 202. Note that the lengths and the radius of the curvatures of the first rods 100 and the second rods 200 illustrated in FIGS. 17 to 27 include an error range of ±5 mm.

As described above, according to the rod group to be used for spinal deformity correction and fusion in the present embodiment, the shapes and sizes of the first rods 100 and the second rods 200 are determined based of data obtained by tracing the shapes of left side rods before implanting the rods into the bodies of 47 patients who underwent posterior spinal correction and fusion using the rods. In this way, using any of the first rods 100 and the second rods 200, the thoracic vertebrae T6 to T8 become the apex of TK and an anatomically normal spinal column arrangement can be easily acquired. Further, when the second rods 200 are used, lumbar lordosis at the lumbar vertebrae L1 to L5 can also be attained. The first rods 100 and the second rods 200 are molded by laminating titanium alloy powders or cobalt chromium alloy powders by electron beam layered manufacturing, and the laminate-molded laminate body is heat treated to eliminate the residual stress in the laminated direction. In this way, the risk of breakage of the first rods 100 and the second rods 200 can be decreased. Further, since the first rods 100 and the second rods 200 are molded in advance, the shapes of the first rods 100 or the second rods 200 to be attached to the left side and the right side of the spinal column can be the same.

Note that the inventors have suggested the importance of the rod shapes in spinal deformity correction and fusion, based on the significant correlation between the bending angle of rods and the angle of TK. The inventors have also disclosed that spring back of rods can be suppressed by increasing the number of resection of the facet joints and inserting screws as many as possible on the concave side (PLOS ONE 2016). Based on such dynamic analyses, a simultaneous double rod rotation technique (SDRRT) has been implemented for a patient with adolescent idiopathic scoliosis (AIS) using left and right rods of which shapes were made identical to acquire an anatomically normal spinal column arrangement (Spine 2018). Further, as described above, with hierarchical cluster analysis on central curve groups, a total of eleven kinds of rod shapes are calculated with the maximum difference value of 5 mm or less, suggesting the possibility of derivation of reasonable rod shape variations.

On the other hand, when a doctor intraoperatively performs bending processing on straight rods using bending tools, there is a risk of chipping the rods by the bending tools or breakage or the rods due to the residual stress. Further, an anatomically normal spinal column arrangement cannot be obtained when the bent rods have shapes that do not match the spinal column of a patient. In the usual course of surgery, rods are bent to align with the curve of scoliosis, and the bent rods are attached to the thoracic vertebrae. Then, the attached rods are rotated to attain kyphosis of the thoracic vertebrae. When the scoliotic apex is located at the thoracic vertebrae T9 to T11 due to AIS, the postoperative apex of the TK is located at the thoracic vertebrae T9 to T11, thus, an anatomically normal spinal column arrangement is hard to be attained and the spinal column arrangement develops, for example, a gibbus like deformity.

Variation

In the above described embodiment, an example where the first rods 100 and the second rods 200 are molded by laminating titanium alloy powders and cobalt-chromium alloy powders by election beam layered manufacturing at the rod making step (step S104) has been described. At the rod making step (step S104), any metal powders for clinical use other than titanium alloy powders and cobalt-chromium alloy powders may be used to mold the first rods 100 and the second rods 200 into the above-described shapes. In addition, at the rod making step (step S104), the first rods 100 and the seconds rod 200 may be made by a method other than electron beam layered manufacturing, such as, by producing straight rods by forging and bending the rods in a mold die and eliminating a residual stress by heat processing after the bending processing.

In the above-described embodiment, an example where the rod group includes eleven kinds of rod shapes has been described. The rod group may include two or more kinds of shapes of rods, at least including the first rod 100 and the second rod 200.

In the above-described embodiment, an example of SDRRT for a patient with AJS has been described. The first rod 100 and the second rod 200 and the spine stabilization system 1 are used not only in SDRRT for AIS but also in other methods for treating scoliosis.

Although, in the above-described embodiment, an example where the coupling device attachment elements are pedicle screws 300 has been described, the coupling device attachment element may be any tool that can fix the first rods 100 or the second rods 200 to the spinal column. For example, the coupling device attachment element may be a hook or a wire for attaching the first rods 100 or the second rods 200 to the spinal column.

In the above-described embodiment, an example where the first rods 100 are used to be attached to a portion of the spinal column including the twelve thoracic vertebrae T1 to T12 of a patient has been described as illustrated in FIG. 2. The first rods 100 may be attached to any plurality of thoracic vertebrae T1 to T12 depending on the condition of a patient, and the first rods 100 may be attached to the thoracic vertebrae T2 or T3 to the thoracic vertebra T12. Alternatively, the first rods 100 may be attached to the lumbar vertebrae L1 and L2 in addition to the thoracic vertebrae. Further, an example where the second rods 200 are attached to a portion of the spinal column including the thoracic vertebrae T1 to T12 and the lumbar vertebrae L1 to L5 of a patient has been described as illustrated in FIG. 3. The second rods 200 may be attached to any of the thoracic vertebrae T1 to T12 and any of the lumbar vertebrae L1 to L5 of a patient depending on the condition of the patient, for example, the second rods 200 may be attached to the thoracic vertebrae T2 or T3 to the lumbar vertebrae L3 or L4.

Figure 28:
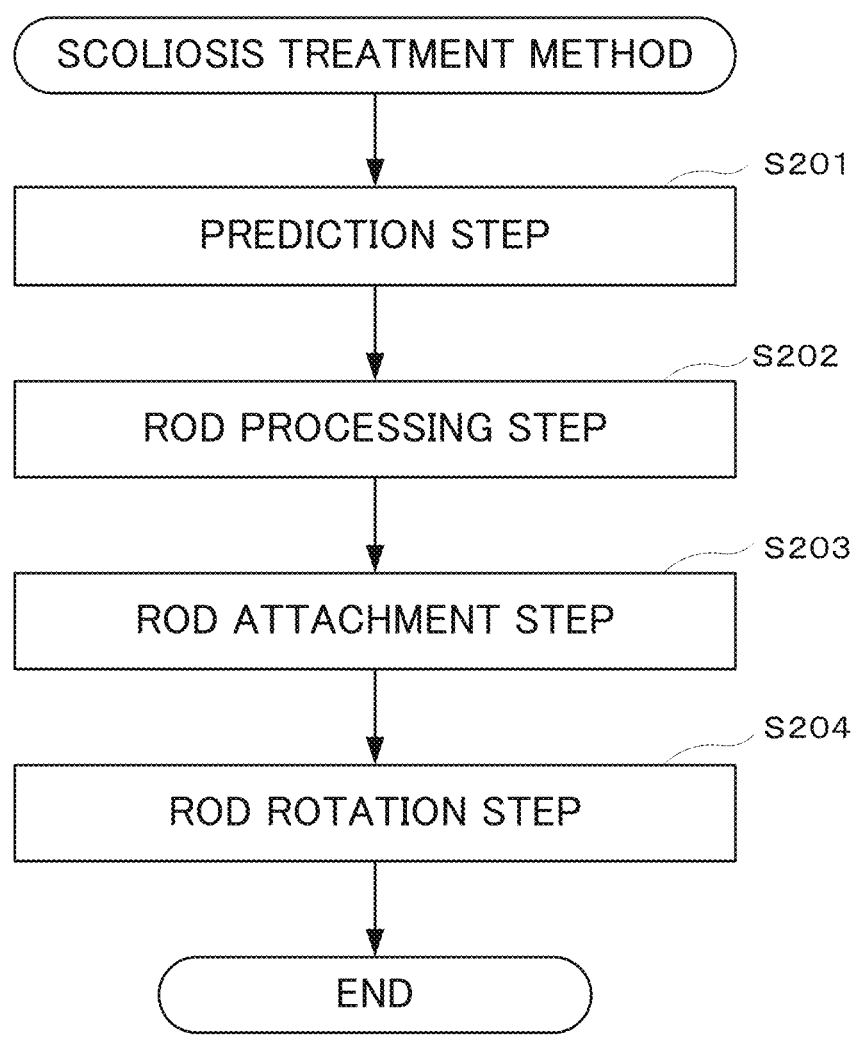
FIG. 28 is a flowchart illustrating a method of treating scoliosis according to a variant of the present disclosure.

In the above described embodiment, an example where the shapes and sizes of the first rods 100 or the second rods 200 are determined based on data obtained by tracing rod shapes before implanting the rods in bodies of patients who underwent posterior correction and fusion has been described. The first rods 100 and the second rods 200 may be any shapes with which an anatomically normal spinal column arrangement can be easily acquired. For example, an anatomically normal spinal column arrangement without thoracic idiopathic scoliosis is predicted for a patient with thoracic idiopathic scoliosis. The first rods 100 or the second rods 200 may be obtained by bending rods into a shape extending along the predicted spinal column arrangement. In such case, the method of treating scoliosis includes, as illustrated in FIG. 28, a prediction step of predicting an anatomically normal spinal column arrangement without thoracic idiopathic scoliosis for a patient with thoracic idiopathic scoliosis (step S201); a rod processing step of bending a pair of rods into a shape extending along the spinal column arrangement as predicted at the prediction step (step S201)(step S202); a rod attachment step of attaching the pair of rods that were bent at the rod processing step (step S202) to the spinal column of a patient (step S203); and a rod rotation step of rotating the attached pair of rods (step S204). According to the method of treating scoliosis, using rods that were bent into a shape predicted at the prediction step (step S201), the thoracic vertebrae T6 to T8 can be the apex of TK and an anatomically normal spinal column arrangement can be easily acquired.

In the prediction step (S201), the anatomically normal spinal column arrangement without thoracic idiopathic scoliosis is predicted on the basis of X-ray images, computed tomography (CT) images, or the like of the spinal column of the patient. At this time, the spinal column arrangement may be predicted that locates the apex of the thoracic kyphosis at the thoracic vertebrae T6 to T8.

In the rod processing step (step S202), any rod processing method may be used that is capable of processing the pair of rods into the shape extending along the predicted spinal arrangement. For example, the rod processing method may be bending processing that uses a bending tool to bend rods such as straight rods. Alternatively, the rod curvatures of the shape extending along the predicted spinal column arrangement may be determined, and the pair of rods may be processed into a shape extending along the spinal column arrangement by using electron beam laminating to laminate titanium alloy powder or cobalt-chromium alloy powder on the basis of the determined rod curvatures.

In the rod attachment step (step S203), the rods may be attached to the spinal column of the patient by resectioning the facet joints of the patient and then attaching the rods by coupling device attachment elements. Due to resectioning of the facet joints of the patient, the curve of the spine of the patient becomes easily made to follow the curve of the rods. Also in the rod attachment step (step S203), the rods 100 having mutually different rod lengths and the rods 200 having mutually different rod lengths included in the rod group may be selected in accordance with lengths of the spine of the patient, and the selected first rods 100 and the selected second rods 200 may be attached to the spine of the patient. When medical treatment to correct the thoracic vertebrae of the patient is possible, the first rods 100 are selected, and when correction of the thoracic vertebrae and the lumbar vertebrae is required, the second rods 200 are selected. In this case, the rod processing step (step S202) can be omitted.

In the rod rotation step (step S204), the attached pair of rods is rotated. Due to such rotation, the apex of the thoracic kyphosis can be guided to the thoracic vertebrae T6 to T8, and the postoperative apex of the thoracic kyphosis can be located at a position different from a preoperative apex of the thoracic kyphosis.

Example

The following will describe an example of the present disclosure in contrast to a control case to demonstrate the effects of the present disclosure. This example indicates an aspect of the present disclosure without limitation thereto.

An example where the above-described first rods 100 are screwed to the vertebrae and held by the pedicle screws 300 by spinal deformity correction and fusion so as to correct and fuse the spinal column to a normal or near-normal state will be described with reference to the drawings.

Figure 29:
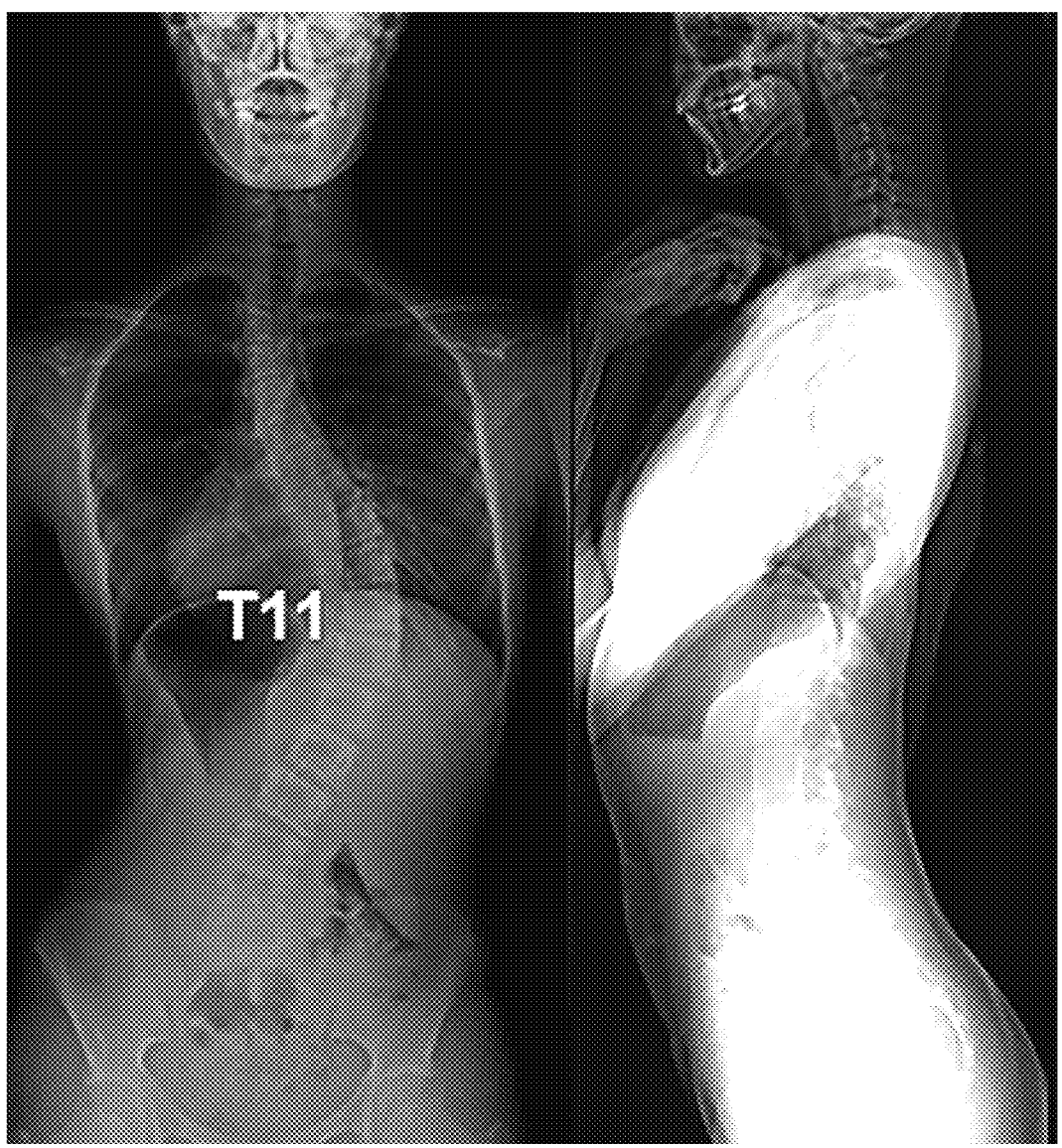
FIG. 29 is an X-ray photograph of a patient with thoracic idiopathic scoliosis.
Figure 30:
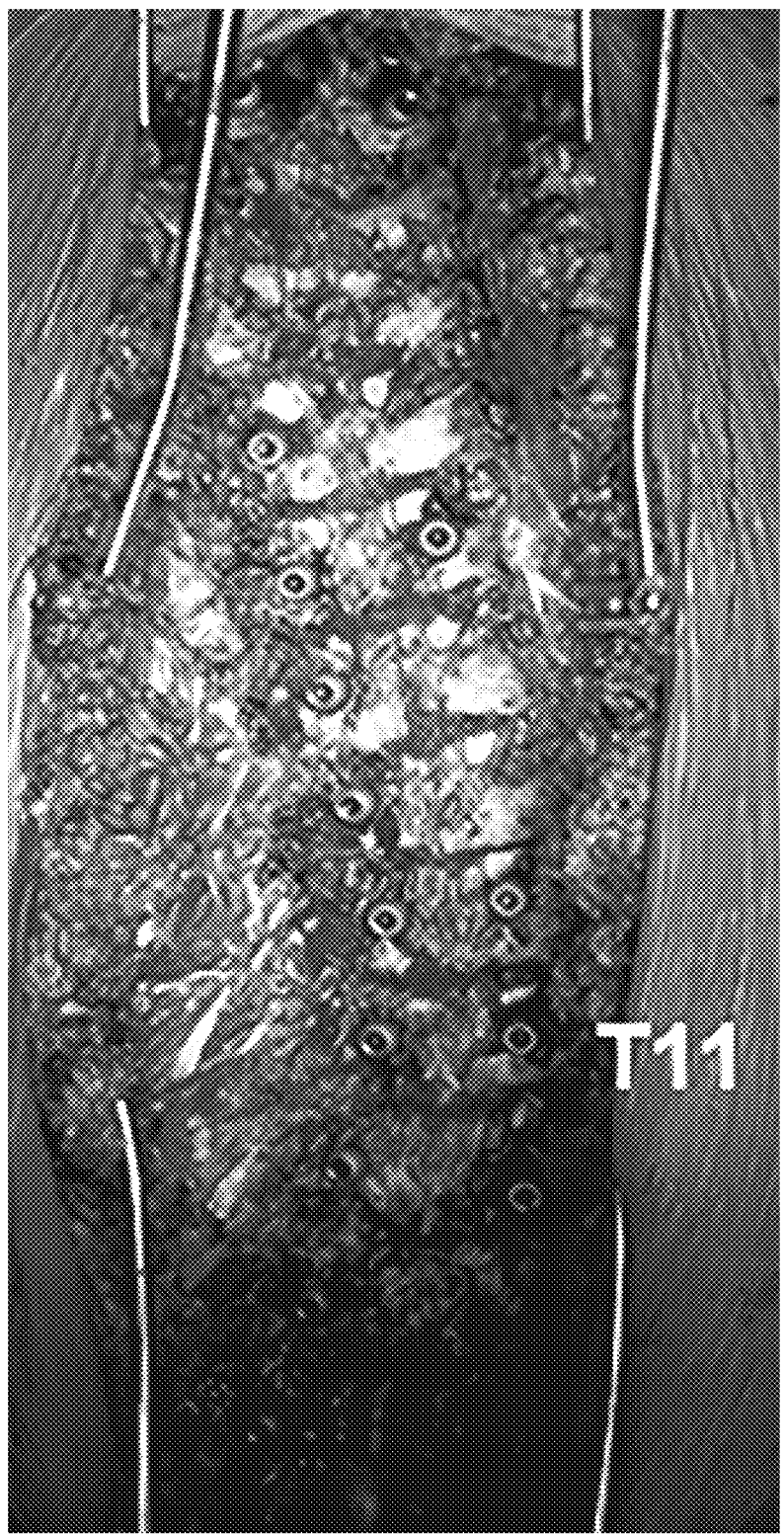
FIG. 30 is an intraoperative photograph of attaching the first rods to the spinal column of a patient using pedicle screws according to an example of the present disclosure.

The subject patient was a 14-year-old girl who developed thoracic AIS exhibiting a single right-sided convex thoracic curve as illustrated in FIG. 29. The main thoracic (MT) curve from the thoracic vertebra T6 to the lumbar vertebra L3 of the patient was 54° and the curve of the TK was 1°. The curve pattern of the patient was Lenke type 1A. The apex of the MT scoliosis was at T11. In the surgery, as illustrated in FIGS. 30 and 31, the above-described pair of first rods 100 were attached to the spinal column of the patient with the pedicle screws 300 that were screwed to the vertebrae. Then, as illustrated in FIG. 32, the attached pair of first rods 100 were simultaneously rotated. The first rods 100 had the above-described shapes, which guided the spinal column to a postoperatively anatomically normal spinal column arrangement (the apex of the TK was located at the thoracic vertebrae T6 to T8).

Figure 33:
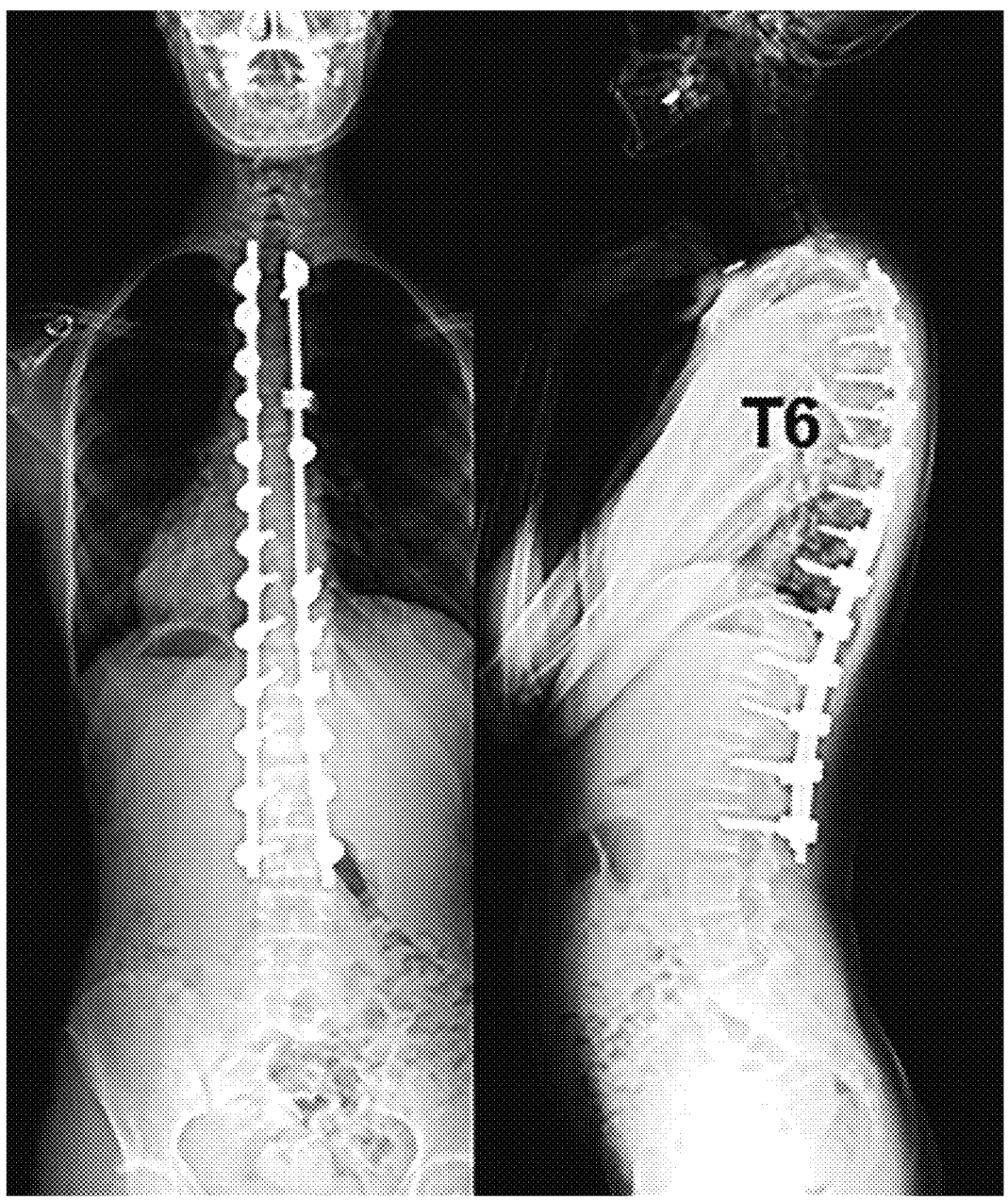
FIG. 33 is an X-ray photograph, two years after the surgery, of a patient implanted with the first rods according to the example of the present disclosure.

In two years after the surgery, as illustrated in FIG. 33, the MT scoliosis angle of the patient was 6° and the angle of the TK was 23°. The apex of the TK was at the thoracic vertebra T6. In this way, using the first rods 100, the thoracic vertebra T6 becomes the apex of the TK, whereby an anatomically normal spinal column arrangement could be easily acquired.

Figure 34:
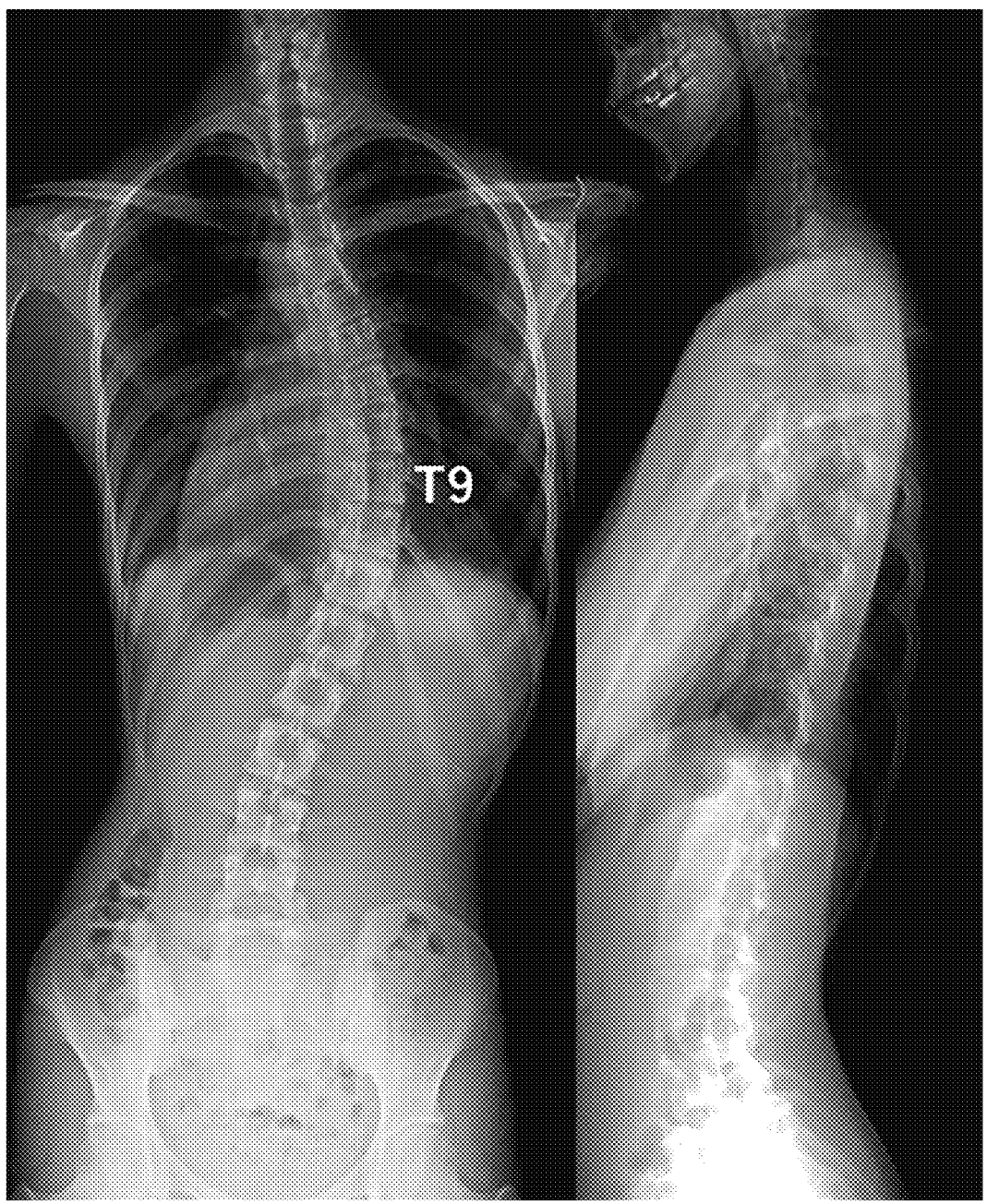
FIG. 34 is an X-ray photograph of a patient with thoracic idiopathic scoliosis.
Figure 35:
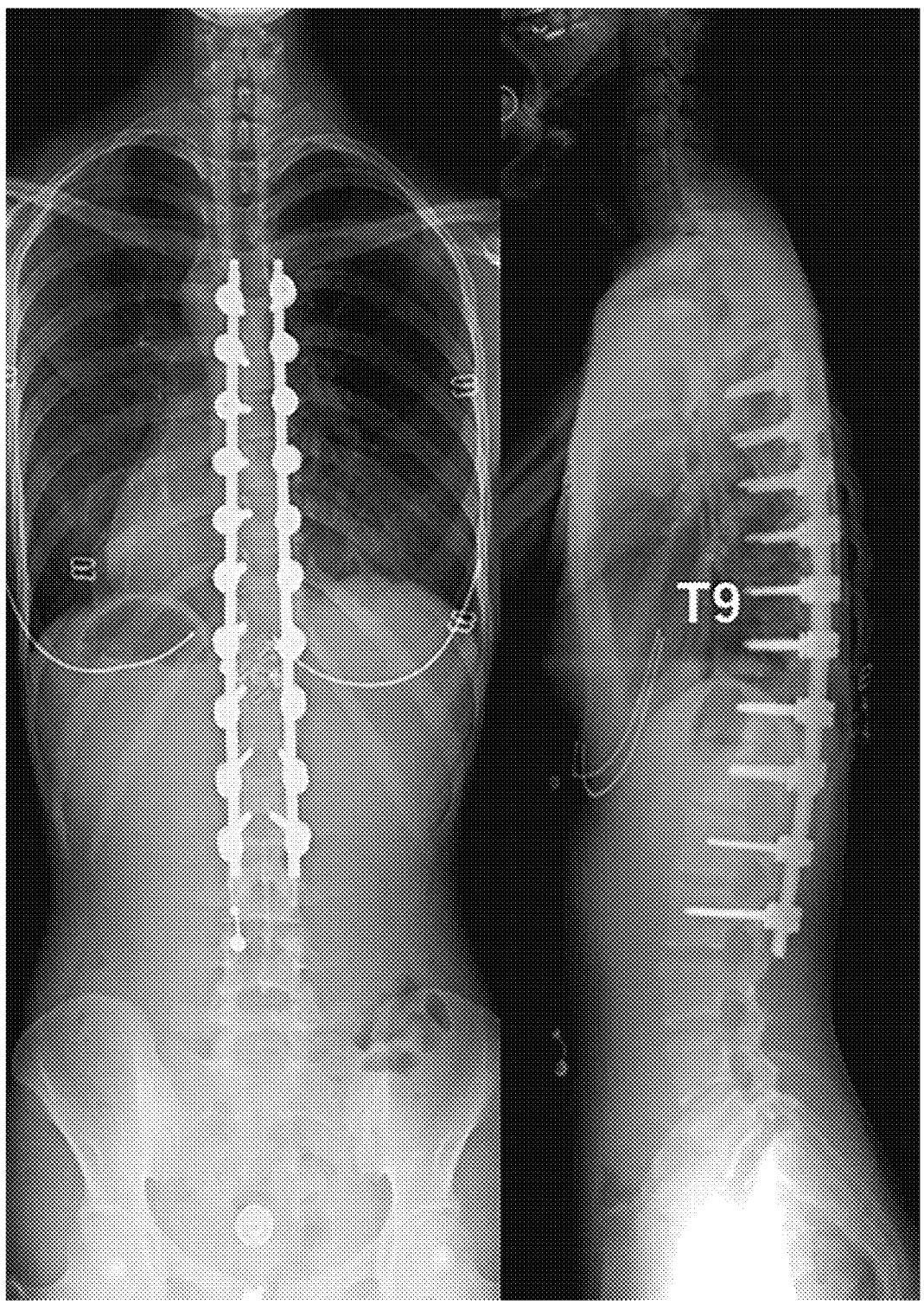
FIG. 35 is a postoperative X-ray photograph of a patient implanted with rods according to a control case.

In contrast, in a control case, a patient developed thoracic AIS and the apex of MT scoliosis was at T9 as illustrated in FIG. 34. The postoperative apex of the TK of the patient was at T9 as illustrated in FIG. 35, which is almost identical with the preoperative apex (T9) of scoliosis. The postoperative "non-anatomical" TK is considered to be created by the procedure of rod bending so as to approximate the curvature of the rods to the curvature of scoliosis of the spinal column before correction, and by attaching the rods to the spinal column of the patient and rotating the rods. Note that the shapes of the rods used in the control case were different from the shapes of the above-described first rods 100 and the second rods 200. In this way, using the rods that were bent to approximate the curvature of the rods to the curvature of scoliosis of the spinal column before correction, the apex of the TK of the patient became T9 that was almost identical with the preoperative apex (T9) of thoracic scoliosis, exhibiting a gibbus like condition instead of an anatomically normal spinal column arrangement.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims priority based on Japanese Patent Application No. 2018-34840 filed Feb. 28, 2018, the entire disclosure of which is incorporated herein by reference.

INDUSTRIAL APPLICABILITY

The present disclosure can provide rods that am used for the purpose of acquiring an anatomically normal spinal column arrangement in spinal deformity correction and fusion.

REFERENCE SIGNS LIST

1 Spine stabilization system
100 First rod
101 Curved section
102 Straight section
200 Second rod
201 First curved section
202 Second curved section
300 Pedicle screw
301 Bone-screw part
302 Tulip shaped head
303 Securing screw
304 Receptacle

The invention claimed is:

1. A rod manufacturing method comprising:
   a rod data acquisition step of acquiring data indicating a plurality of previous rod shapes that were bent into shapes extending along anatomically normal spinal column arrangements;
   a length classification step of classifying data indicating the previous rod shapes acquired at the rod data acquisition step into groups of rod lengths with a difference of reference length;
   a rod shape acquisition step of acquiring data indicating best-fit curves from the previous rod shapes included in groups classified at the length classification step; and
   a rod making step of making rods used in spinal deformity correction and fusion, according to the best-fit curves acquired at the rod shape acquisition step.

2. A method for treatment of scoliosis comprising:
   a prediction step of predicting an anatomically normal spinal column arrangement without thoracic idiopathic scoliosis for a patient with thoracic idiopathic scoliosis;
   a rod attachment step of attaching to the spinal column of the patient a pair of rods having shapes extending along the spinal column arrangement predicted in the prediction step;
   a rod rotation step of rotating the attached pair of rods; and
   guiding the postoperative apex of the thoracic kyphosis to the thoracic vertebrae T6 to T8 and the postoperative apex to a position different from a preoperative apex of the thoracic kyphosis.

3. The method for treatment of scoliosis according to claim 2, wherein in the
   prediction step, the spinal column arrangement is predicted for which the apex of the thoracic kyphosis is located at the thoracic vertebrae T6 to T8.

4. The method for treatment of scoliosis according to claim 2, wherein in the rod attachment step the facet joints are resectioned, and the rods are attached to the spinal column of the patient by coupling device attachment elements.

5. The method for treatment of scoliosis according to claim 2, wherein in the rod attachment step,
   a plurality of first rods and a plurality of second rods are selected to match lengths of the spinal column of the patient, the first rods having an arcuate first curve and mutually different lengths, the second rods having an S-shaped second curve and mutually different lengths, and
   the selected first rods or second rods are attached to the spinal column of the patient.

6. The method for treatment of scoliosis according to claim 5, wherein
   the first rods have (i) in a shape extending along thoracic kyphosis of an anatomically normal spinal column arrangement, a curved section and a straight section to be attached to thoracic vertebrae, or (ii) in a shape extending along thoracic kyphosis of an anatomically normal spinal column arrangement, a curved section and reverse curved section to be attached to thoracic vertebrae, the second rods have (i) in a shape extending along thoracic kyphosis of an anatomically normal spinal column arrangement, a first curved section to be attached to the thoracic vertebrae, and (ii) in a shape extending along lumbar lordosis of an anatomically normal spinal column arrangement, a second curved section to be attached to lumbar vertebrae, the first rods and the second rods having shapes for (i) guiding a postoperative apex of the thoracic kyphosis to be located at the thoracic vertebrae T6 to T8, and (ii) guiding the postoperative apex of the thoracic kyphosis to be located at a position different from a preoperative apex of the thoracic kyphosis.

7. The method for treatment of scoliosis according to claim 2, further comprising:

a rod processing step of processing the pair of rods into a shape extending along the spinal column arrangement predicted in the prediction step.

8. The method for treatment of scoliosis according to claim 7, wherein the rod processing step comprises:

a layering step of lamination into rod-shaped laminate bodies by layered manufacturing; and a heat treatment step of heat treating to eliminate residual stresses in a lamination direction of the rod-shaped laminate bodies.

* * * * *